(12) United States Patent
Schneider et al.

(10) Patent No.: US 8,939,876 B2
(45) Date of Patent: Jan. 27, 2015

(54) METHOD AND APPARATUS FOR ASSEMBLING DISPOSABLE ABSORBENT ARTICLES

(75) Inventors: Uwe Schneider, Cincinnati, OH (US); Yoichiro Yamamoto, Cologne (DE)

(73) Assignee: The Procter & Gamble Company, Cincinnati, OH (US)

( * ) Notice: Subject to any disclaimer, the term of this patent is extended or adjusted under 35 U.S.C. 154(b) by 605 days.

(21) Appl. No.: 13/311,962

(22) Filed: Dec. 6, 2011

(65) Prior Publication Data
US 2012/0157281 A1 Jun. 21, 2012

Related U.S. Application Data

(60) Provisional application No. 61/424,702, filed on Dec. 20, 2010.

(51) Int. Cl.
*B31F 1/00* (2006.01)
*A61F 13/15* (2006.01)
*A61F 13/496* (2006.01)

(52) U.S. Cl.
CPC ......... *A61F 13/15756* (2013.01); *A61F 13/496* (2013.01); *A61F 13/15739* (2013.01); *A61F 13/15747* (2013.01); *A61F 13/15764* (2013.01)
USPC ... 493/379; 604/358; 604/385.04; 604/385.3; 604/396; 156/258

(58) Field of Classification Search
CPC ........... B31F 1/00; A61F 13/15; A61F 13/20; A61F 13/15585; A61F 13/49; A61F 13/496; A61F 13/49058; A61F 13/49061
USPC .................. 493/379, 125, 151; 604/393, 385, 604/385.21, 385.04, 385.3, 385.29, 355, 604/378, 358; 156/297, 604, 428, 258, 265, 156/539, 173, 292, 147
See application file for complete search history.

(56) References Cited

U.S. PATENT DOCUMENTS

| | | | |
|---|---|---|---|
| 3,905,592 A * | 9/1975 | Spencer et al. | ............... 493/422 |
| 3,929,135 A | 12/1975 | Thompson | |
| 4,324,246 A | 4/1982 | Mullane et al. | |
| 4,342,314 A | 8/1982 | Radel et al. | |
| 4,463,045 A | 7/1984 | Ahr et al. | |
| 4,523,969 A * | 6/1985 | Spencer | ........................ 156/161 |
| 4,609,518 A | 9/1986 | Curro et al. | |
| 4,610,678 A | 9/1986 | Weisman et al. | |

(Continued)

FOREIGN PATENT DOCUMENTS

| | | |
|---|---|---|
| EP | 0 565 606 B1 | 3/1995 |
| WO | WO 93/25172 | 12/1993 |

(Continued)

OTHER PUBLICATIONS

PCT International Search Report dated May 11, 2012, 9 pages.

*Primary Examiner* — Thanh Truong
*Assistant Examiner* — Eduardo R Ferrero
(74) *Attorney, Agent, or Firm* — Charles R. Matson

(57) ABSTRACT

A method of manufacturing an absorbent article in a diaper manufacturing machine, the method includes providing a chassis, folding the chassis along one or more axes, providing two side panels, aligning the side panels with the chassis, and attaching the side panels to the chassis along four seams. The method may include forming the four seams substantially simultaneously.

18 Claims, 13 Drawing Sheets

(56) References Cited

U.S. PATENT DOCUMENTS

| | | | |
|---|---|---|---|
| 4,629,643 A | 12/1986 | Curro et al. | |
| 4,673,402 A | 6/1987 | Weisman et al. | |
| 4,695,278 A | 9/1987 | Lawson | |
| 4,795,454 A | 1/1989 | Dragoo | |
| 4,834,735 A | 5/1989 | Alemany et al. | |
| 4,888,231 A | 12/1989 | Angstadt | |
| 4,968,312 A | 11/1990 | Khan | |
| 4,988,344 A | 1/1991 | Reising et al. | |
| 4,988,345 A | 1/1991 | Reising | |
| 4,990,147 A | 2/1991 | Freeland | |
| 5,006,394 A | 4/1991 | Baird | |
| 5,062,840 A | 11/1991 | Holt et al. | |
| 5,137,537 A | 8/1992 | Herron et al. | |
| 5,147,345 A | 9/1992 | Young et al. | |
| 5,171,236 A | 12/1992 | Dreier et al. | |
| 5,260,345 A | 11/1993 | DesMarais et al. | |
| 5,269,755 A | 12/1993 | Bodicky | |
| 5,306,266 A | 4/1994 | Freeland | |
| 5,342,338 A | 8/1994 | Roe | |
| 5,387,207 A | 2/1995 | Dyer et al. | |
| 5,397,318 A | 3/1995 | Dreier | |
| 5,514,121 A | 5/1996 | Roe et al. | |
| 5,540,671 A | 7/1996 | Dreier | |
| 5,554,142 A | 9/1996 | Dreier et al. | |
| 5,562,646 A | 10/1996 | Goldman et al. | |
| 5,571,096 A | 11/1996 | Dobrin et al. | |
| 5,620,431 A * | 4/1997 | LeMahieu et al. | 604/385.25 |
| 5,650,222 A | 7/1997 | DesMarais et al. | |
| 5,653,703 A | 8/1997 | Roe et al. | |
| 5,669,894 A | 9/1997 | Goldman et al. | |
| 5,716,478 A * | 2/1998 | Boothe et al. | 156/302 |
| 5,733,401 A * | 3/1998 | Linman et al. | 156/160 |
| 5,772,825 A * | 6/1998 | Schmitz | 156/164 |
| 5,779,831 A | 7/1998 | Schmitz | |
| 5,858,151 A * | 1/1999 | Igaue et al. | 156/164 |
| 5,865,823 A | 2/1999 | Curro | |
| 5,941,864 A | 8/1999 | Roe | |
| 6,010,491 A | 1/2000 | Roe et al. | |
| 6,414,215 B1 | 7/2002 | Roe | |
| 6,441,266 B1 | 8/2002 | Dyer et al. | |
| 6,443,938 B1 * | 9/2002 | Vogt | 604/391 |
| 6,482,191 B1 | 11/2002 | Roe et al. | |
| 6,497,032 B2 * | 12/2002 | Maxton et al. | 29/429 |
| 6,573,423 B1 | 6/2003 | Herrlein et al. | |
| 6,656,312 B1 * | 12/2003 | Schmitz et al. | 156/265 |
| 6,723,035 B2 | 4/2004 | Franklin et al. | |
| 6,776,316 B2 | 8/2004 | Van Eperen et al. | |
| 6,984,279 B2 * | 1/2006 | Mortell et al. | 156/211 |
| 7,039,997 B2 | 5/2006 | Vogt et al. | 29/449 |
| 7,195,586 B2 * | 3/2007 | Yamamoto et al. | 493/429 |
| 7,322,925 B2 | 1/2008 | Couillard et al. | |
| 7,347,914 B2 * | 3/2008 | Umebayashi et al. | 156/302 |
| 7,387,148 B2 * | 6/2008 | Vogt et al. | 156/480 |
| 7,591,811 B2 * | 9/2009 | Crislip Wilkinson | 604/385.25 |
| 7,617,656 B2 * | 11/2009 | Wiedmann | 53/429 |
| 7,744,576 B2 | 6/2010 | Busam et al. | |
| 7,750,203 B2 | 7/2010 | Becker et al. | |
| 7,753,099 B2 | 7/2010 | Schneider et al. | |
| 2003/0205312 A1 * | 11/2003 | Tomsovic et al. | 156/227 |
| 2004/0236304 A1 * | 11/2004 | Coates et al. | 604/393 |
| 2005/0067093 A1 * | 3/2005 | Goda et al. | 156/265 |
| 2005/0131380 A1 * | 6/2005 | Suzuki et al. | 604/392 |
| 2005/0177124 A1 * | 8/2005 | Kondo | 604/385.29 |
| 2006/0108054 A1 | 5/2006 | Ukegawa | |
| 2008/0083489 A1 * | 4/2008 | Schneider et al. | 156/258 |
| 2008/0132873 A1 * | 6/2008 | Glaug | 604/386 |
| 2008/0134487 A1 * | 6/2008 | Hartono | 29/428 |
| 2008/0210067 A1 * | 9/2008 | Schlinz et al. | 83/23 |
| 2008/0249493 A1 * | 10/2008 | Kobayashi et al. | 604/378 |
| 2008/0275420 A1 * | 11/2008 | Ishikawa | 604/385.29 |
| 2009/0275910 A1 * | 11/2009 | Schmitz | 604/385.28 |
| 2009/0326417 A1 * | 12/2009 | Ales et al. | 600/584 |
| 2010/0050411 A1 * | 3/2010 | Yamamoto | 29/428 |
| 2010/0094236 A1 * | 4/2010 | Schmitz | 604/385.01 |
| 2010/0236703 A1 * | 9/2010 | Schneider et al. | 156/258 |
| 2011/0208144 A1 * | 8/2011 | Roe et al. | 604/366 |
| 2012/0157281 A1 * | 6/2012 | Schneider et al. | 493/379 |

FOREIGN PATENT DOCUMENTS

| | | |
|---|---|---|
| WO | WO 94/14395 | 7/1994 |
| WO | WO 95/16746 | 6/1995 |
| WO | WO 00/41664 | 7/2000 |
| WO | WO 03/094815 A1 | 12/2004 |
| WO | WO 2006/015141 | 2/2006 |
| WO | WO 2008/147270 A1 | 12/2008 |

* cited by examiner

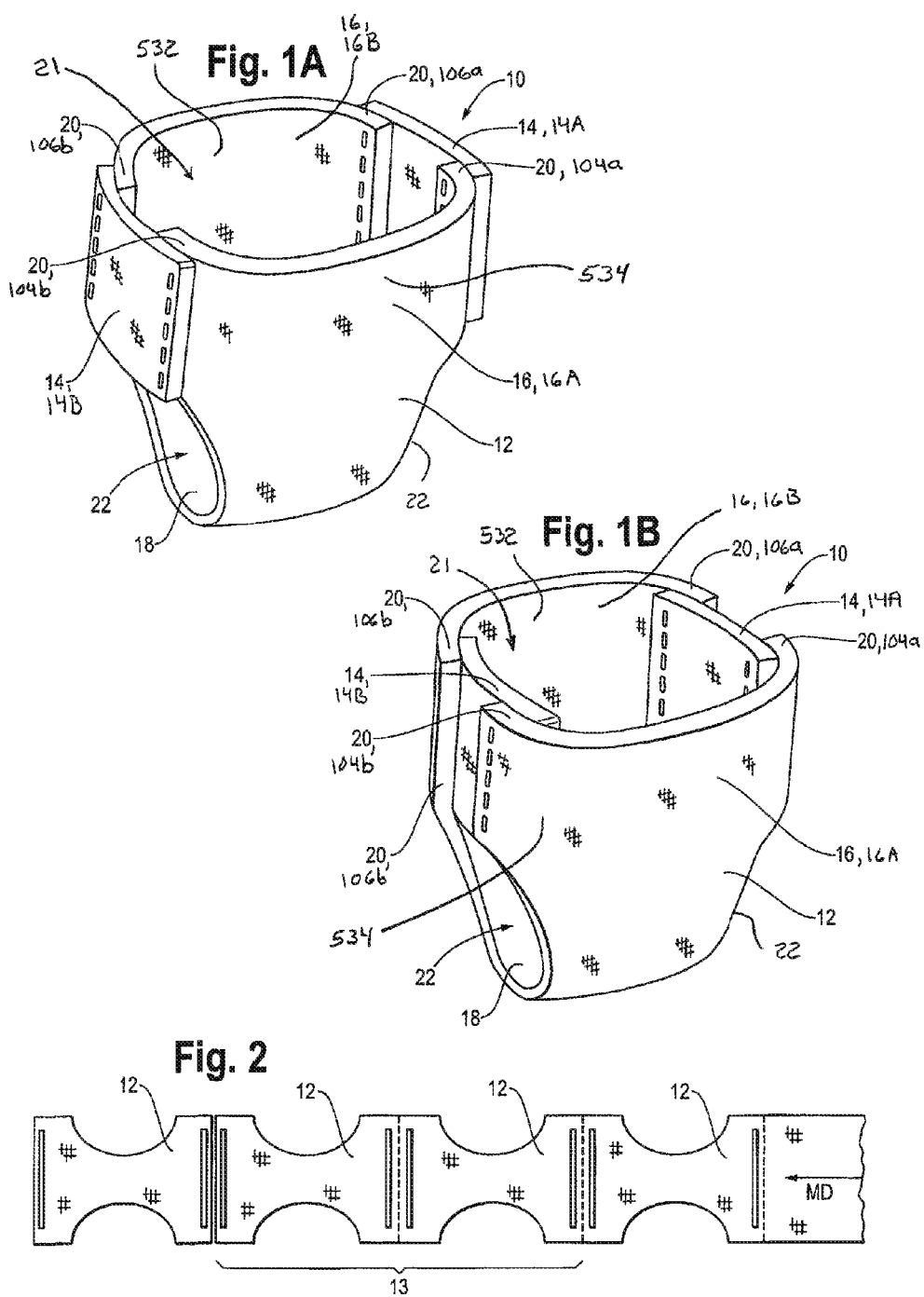

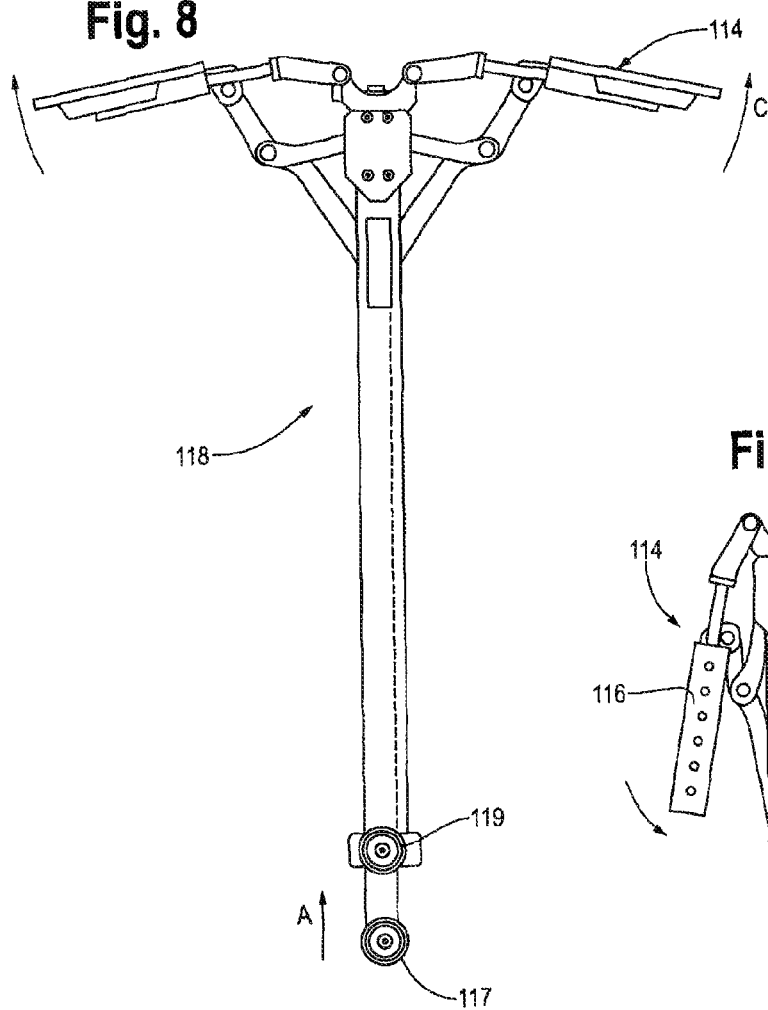
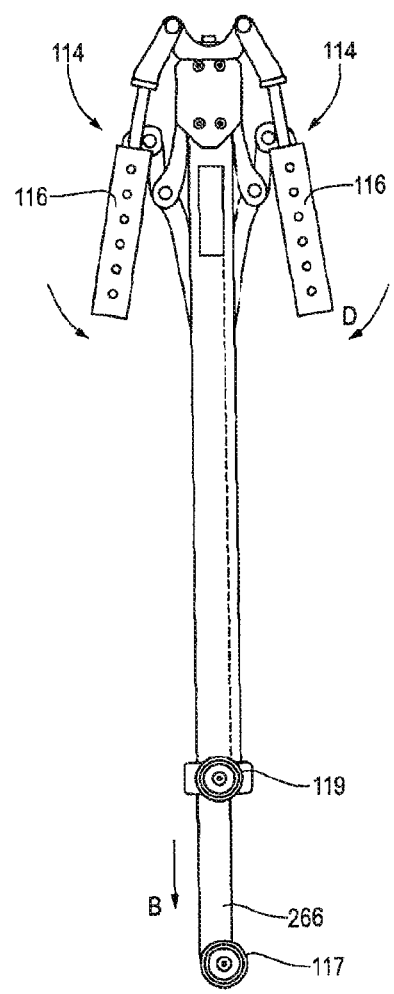

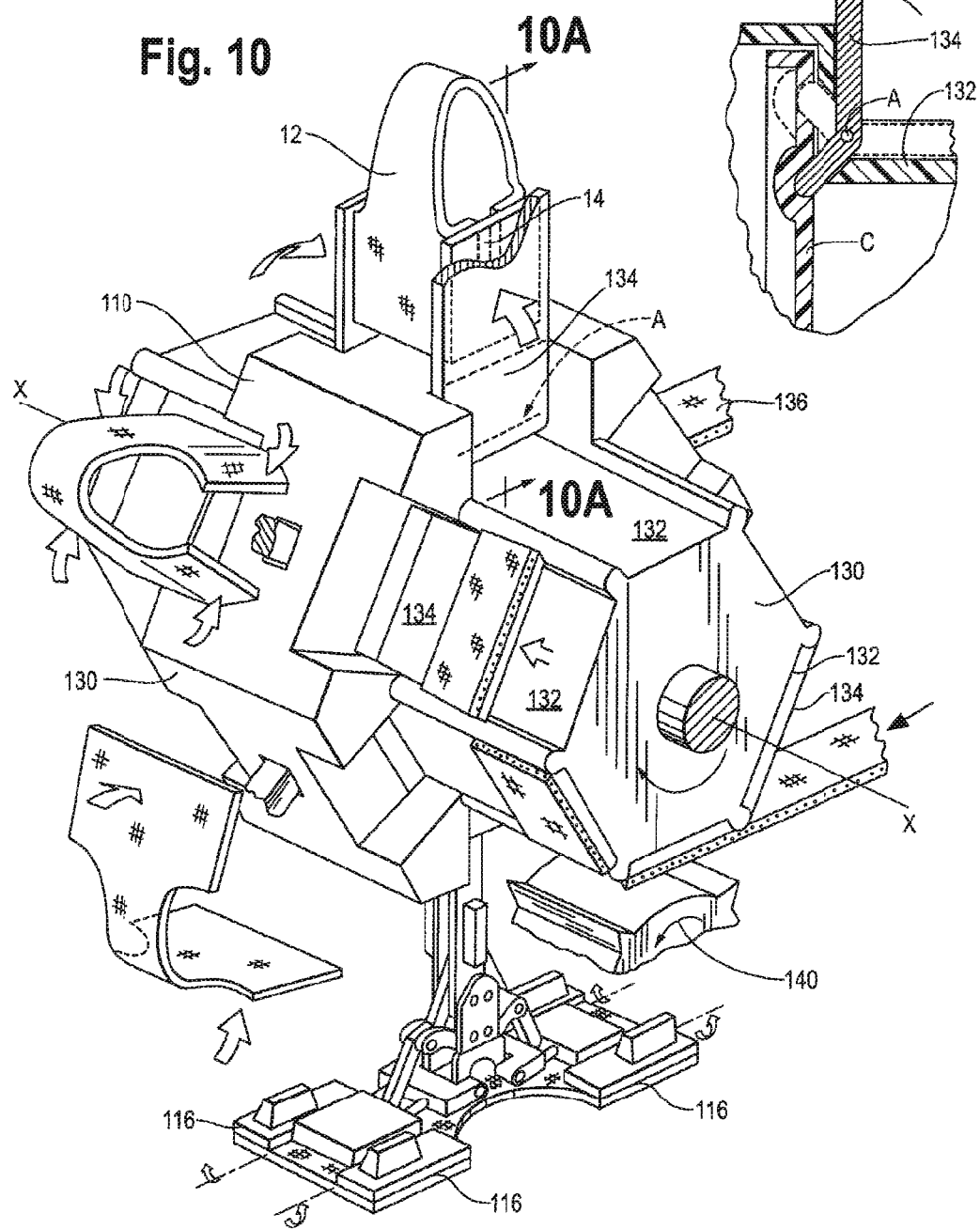

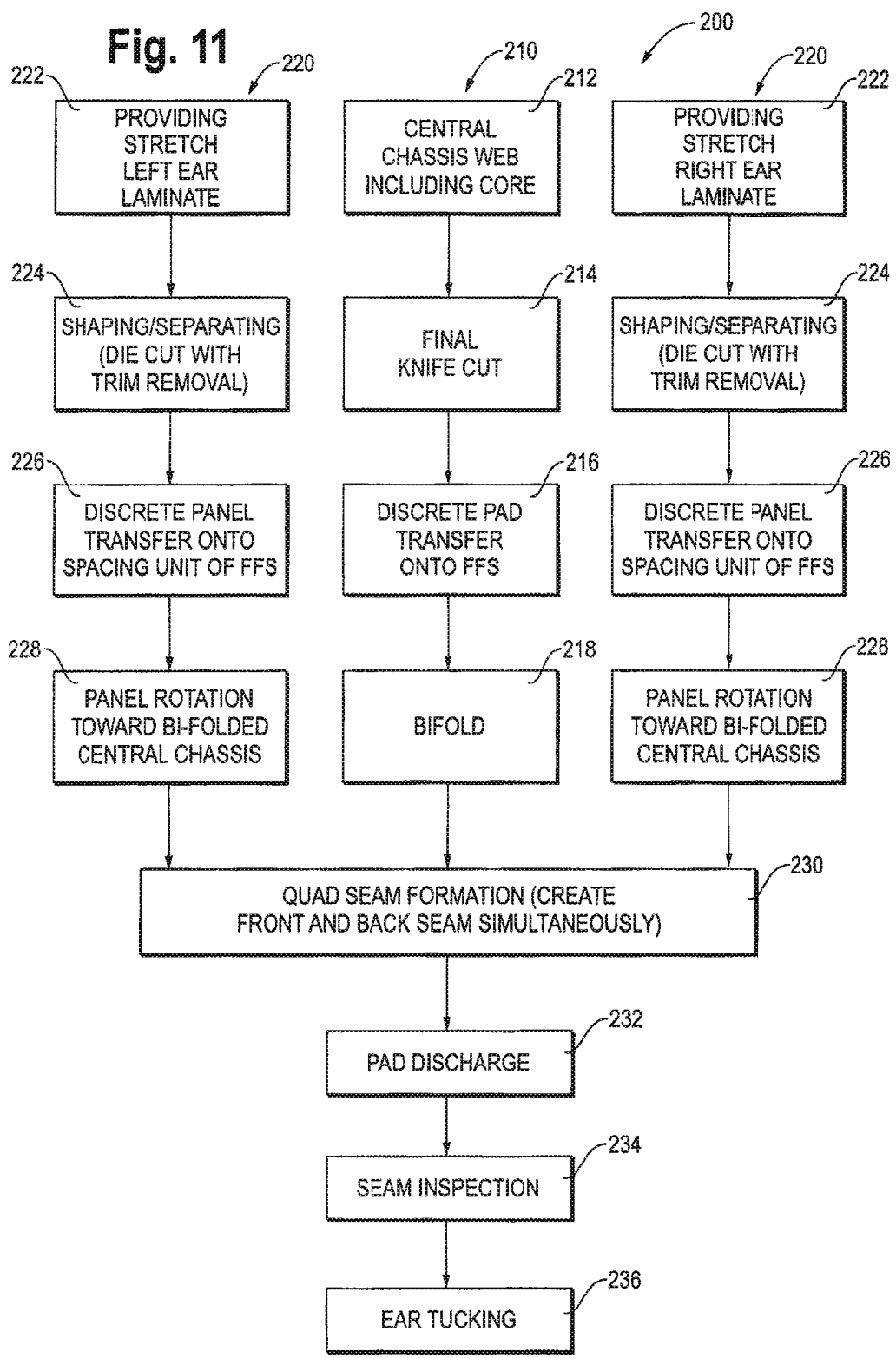

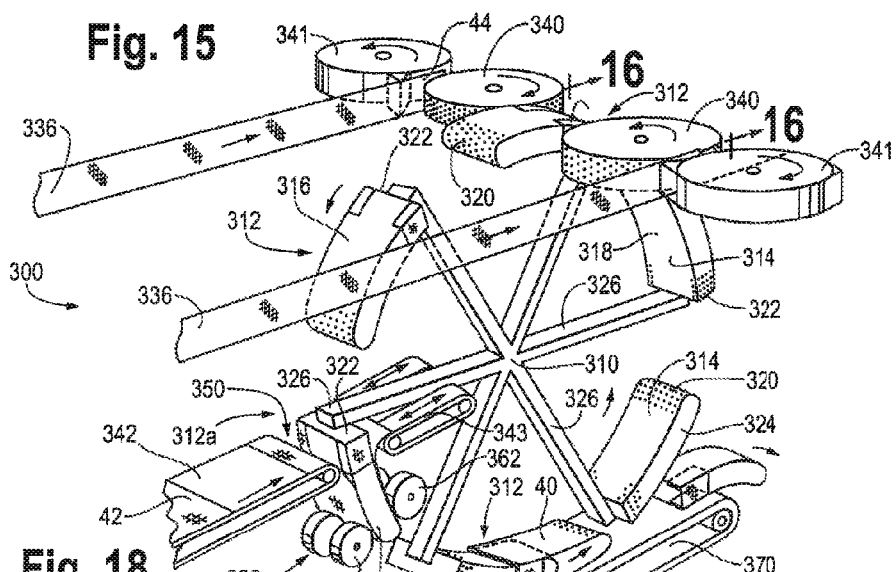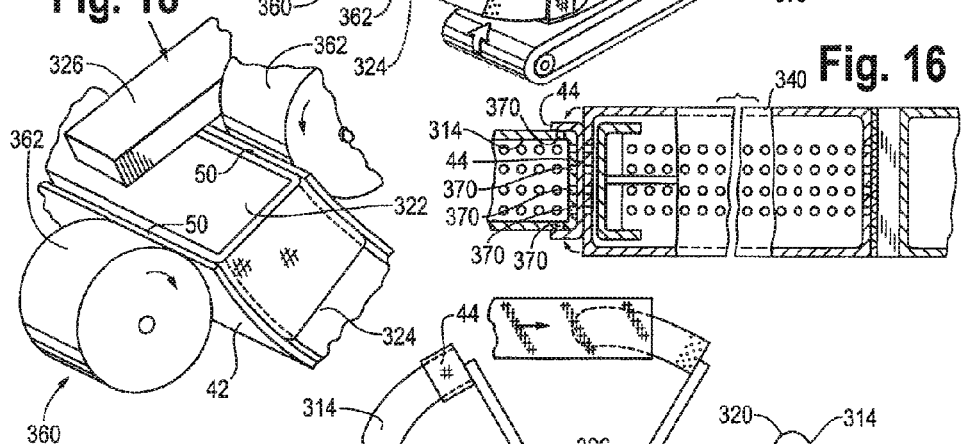

METHOD AND APPARATUS FOR ASSEMBLING DISPOSABLE ABSORBENT ARTICLES

CROSS REFERENCE TO RELATED APPLICATION

This application claims the benefit of U.S. Provisional Application No. 61/424,702, filed on Dec. 20, 2010, which is incorporated herein by reference.

FIELD OF THE INVENTION

The present disclosure is generally related to methods and devices for attaching at least two separate webs of material to one another along four separate seams simultaneously, or substantially simultaneously. More particularly, the present disclosure is related to methods and devices for attaching two separate side panels to a diaper chassis along four separate seams.

BACKGROUND OF THE INVENTION

Infants and other incontinent individuals wear disposable absorbent articles such as diapers to absorb and retain urine and other body exudates. Absorbent articles may function both to contain the discharged materials and to isolate these materials from the body of the wearer and from the wearer's garments and bed clothing.

Diapers can be configured to fit on a wearer's body in various ways. For example, some diapers may be configured as pull-on pant-type diapers or training pants. Diapers, such as training pants, may be used with infants prior to and/or during toilet training. Training pants may be configured with a "closed" chassis configuration, in which the chassis is adapted to be pulled on over the legs and lower torso of the wearer without any additional fastening steps.

Closed chassis diapers may be manufactured with a front edge of the chassis being seamed to a back edge of the chassis to form the closed chassis. In some configurations, closed chassis diapers may also have manually tearable side seams. The side seams may be configured as butt-type seams or overlapping side seams.

During the manufacturing process, a closed chassis diaper may be manufactured from a blank cut to a particular configuration and size. Manufacturing processes may involve some type of sealing step to create side seams in the diapers. For example, after being fully assembled, the blank may be folded along a central transverse area and the sides of the front and rear panels are seamed together to form a closed chassis diaper. In other processes, the side seams may be formed by folding the chassis in a crotch portion so that longitudinal edges of the front portion and rear portion are superposed to form seaming areas, which are then treated with ultrasonic energy to sever the material in the seaming area in a first area while simultaneously bonding the material of the seaming area in a marginal area adjacent the first area to form a flangeless seam.

In some manufacturing configurations, the seaming and folding operations may be performed automatically on a processing wheel having a plurality of folding stations and associated seaming mechanisms. Various types of such processing wheels have been described in U.S. Patent Publication No. 2008/0083489 and U.S. Pat. Nos. 5,779,831 and 7,322,925, each of which is incorporated herein by reference.

SUMMARY OF THE INVENTION

A method of manufacturing an absorbent article in a diaper manufacturing machine, the method includes providing a chassis, folding the chassis along one or more axes, providing two side panels, aligning the side panels with the chassis, and attaching the side panels to the chassis along four seams. The method may include forming the four seams substantially simultaneously. Various embodiments of the machinery having the capability to perform the manufacturing methods of the present disclosure are also described herein.

In one form, a method for assembling disposable diaper pants, each diaper pant comprising a chassis, a first side panel, and a second side panel, each chassis having a longitudinal axis and a lateral axis, and comprising a first waist region longitudinally opposed to a second waist region, and a crotch region longitudinally intermediate of the first and second waist regions, each chassis further comprising: a topsheet, a backsheet, and an absorbent core disposed between the topsheet and the backsheet, the method comprising the steps of: providing a chassis; folding the chassis along the lateral axis to position the first waist region into a facing relationship with the second waist region; providing first and second side panels; connecting the first and second side panels with the first waist region and the second waist region of the folded chassis along four seams to form a waist opening and a pair of leg openings; and wherein the four seams are substantially simultaneously produced.

BRIEF DESCRIPTION OF THE DRAWINGS

FIG. 1A is a perspective view of a diaper pant made in accordance with a first embodiment of the present disclosure.

FIG. 1B is a perspective view of a diaper pant made in accordance with a second embodiment of the present disclosure.

FIG. 2 is a top plan view of a web from which pre-forms of chassis employed in the manufacture of the diaper pant of FIG. 1A or FIG. 1B are cut, illustrated as being formed in a machine direction.

FIG. 8 is a side view of the articulator arm of FIG. 7 in an extended configuration.

FIG. 9 is a side view of the articulator arm of FIG. 7 in a retracted configuration.

FIG. 10 is a perspective view of the machine of FIG. 6.

FIG. 10A is a cross-sectional view, taken along lines 10A-10A of FIG. 10.

FIG. 11 is a logic chart schematically illustrating a method of manufacturing a diaper pant according to the teachings of a first embodiment of the present disclosure.

FIG. 15 is a perspective view of a machine that assembles diaper pants according to an alternate embodiment of the present disclosure.

FIG. 16 is a cross-sectional view, taken along lines 16-16 of FIG. 15, of a rear portion of one mandrel of the machine of FIG. 15, together with a supply wheel.

FIG. 17 is a side view of the machine of FIG. 15.

FIG. 18 is an enlarged perspective view of one of the mandrels of the machine of FIG. 15 as a trailing end of the mandrel is passing between securing rollers.

DETAILED DESCRIPTION OF THE INVENTION

Figure 1C:
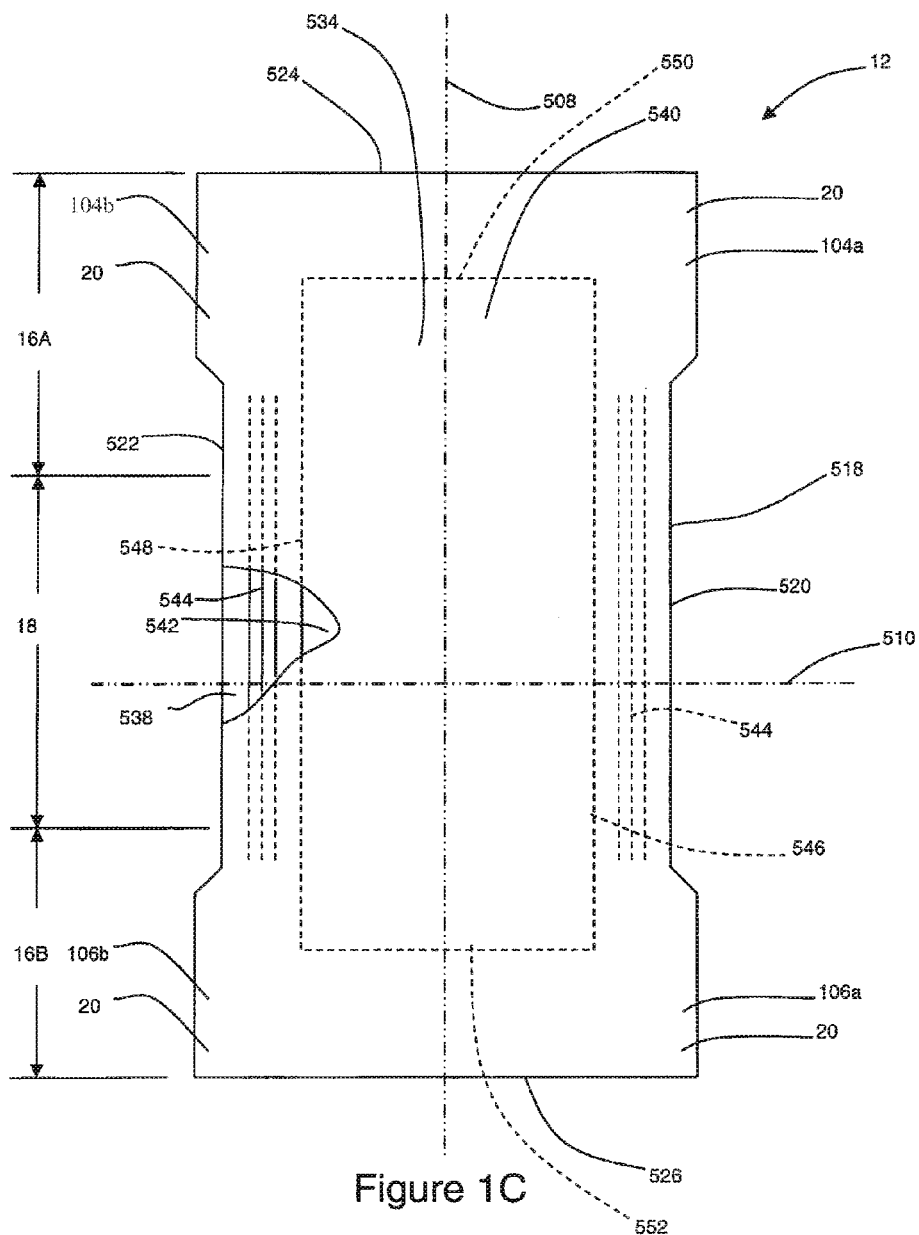
FIG. 1C is a partially cut away plan view of a diaper chassis.

The following term explanations may be useful in understanding the present disclosure:

"Absorbent article" is used herein to refer to consumer products whose primary function is to absorb and retain soils and wastes. "Diaper" is used herein to refer to an absorbent article generally worn by infants and incontinent persons about the lower torso.

The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

The term "pant" (also referred to as "training pant", "preclosed diaper", "diaper pant", "pant diaper", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer. A pant can be preformed by various techniques including, but not limited to, joining together portions of the article using any refastenable and/or permanent closure member (e.g., seams, heat bonds, pressure welds, adhesives, cohesive bonds, mechanical fasteners, etc.).

The term "disposed" is used herein to mean that an element(s) is formed (joined and positioned) in a particular place or position as a macro-unitary structure with other elements or as a separate element joined to another element.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

The term "substrate" or "web" is used herein to describe a material which is primarily two-dimensional (i.e. in an XY plane) and whose thickness (in a Z direction) is relatively small (i.e. 1/10 or less) in comparison to its length (in an X direction) and width (in a Y direction). Non-limiting examples of substrates include a layer or layers or fibrous materials, films and foils such as plastic films or metallic foils that may be used alone or laminated to one or more layers, films and/or foils.

The term "nonwoven" refers herein to a material made from continuous (long) filaments (fibers) and/or discontinuous (short) filaments (fibers) by processes such as spunbonding, meltblowing, and the like. Nonwovens do not have a woven or knitted filament pattern.

The term "machine direction" (MD) is used herein to refer to the direction of material flow through a process.

The term "cross direction" (CD) is used herein to refer to a direction that is generally perpendicular to the machine direction.

The terms "activating", "activation" or "mechanical activation refer to the process of making a substrate, or an elastomeric laminate more extensible than it was prior" to the process.

The term "substantially simultaneously" means events that happen within approximately 1 second or less from one another.

"Live stretch" includes stretching elastic and bonding the stretched elastic to a substrate. After bonding, the stretched elastic is released causing it to contract, resulting in a "corrugated" substrate. The corrugated substrate can stretch as the corrugated portion is pulled to about the point that the substrate reaches at least one original flat dimension. However, if the substrate is also elastic, then the substrate can stretch beyond the relaxed length of the substrate prior to bonding with the elastic. The elastic is stretched at least 25% of its relaxed length when it is bonded to the substrate.

Aspects of the present disclosure relate to methods and apparatuses for manufacturing absorbent articles (e.g., diaper pants) having one or more side panels attached to a diaper chassis, and more particularly, apparatuses and methods utilizing multiple processing stations for processing absorbent articles and being configurable to move along various predetermined travel paths while simultaneously, or substantially simultaneously, attaching the side panels to the chassis along one or more seams. Particular embodiments of apparatuses and methods of manufacture disclosed herein include a processing wheel having a plurality of processing stations which orbit around a rotation axis. The processing stations may be configured to perform various types of operations associated with the manufacture of absorbent articles while the processing stations orbit around the rotation axis. For example, in some embodiments, separate pre-forms, blanks or chassis, from which absorbent articles are formed, may be transferred to the orbiting processing stations from another apparatus used in the manufacturing process, such as an anvil roll or a conveyor belt. As the processing stations move along an orbit path, the processing stations may perform various operations, such as folding the blanks and superimposing sealing areas on the folded blanks. The processing stations may also move the sealing areas into a position in a desired registration or alignment with a sealing station where the sealing areas are connected. Once the processing stations have performed the required operations, the folded blanks in the form of absorbent articles may be moved from the processing wheel to another apparatus used in the manufacturing operation.

For the purposes of a specific illustration, FIGS. 1A and 1B show examples of a diaper pant 10 including a chassis 12 and opposing first and second side panels 14A, 14B. FIG. 1C shows the chassis 12 in a flat, unfolded condition, with the portion of the chassis 12 that faces away from a wearer oriented towards the viewer. A portion of the chassis structure is cut-away in FIG. 1C to more clearly show the construction of and various features that may be included in embodiments of the diaper pant 10.

To provide a frame of reference for the present discussion, the chassis 12 is shown with a longitudinal axis 508 and a lateral axis 510. The chassis 12 is shown as having a first waist region 16A, a second waist region 16B, and a crotch region 18 disposed intermediate the first and second waist regions. The periphery of the chassis 518 is defined by a first longitudinal side edge 520, a second longitudinal side edge 522; a first waist end edge 524 disposed in the first waist region 16A; and a second waist end edge 526 disposed in the second waist region 16B. As shown in FIG. 1, the first and second side panels 14A, 14B connect the first waist region 16A with the second waist region 16B of the chassis 12 to form a waist opening 21 and two leg openings 22.

As shown in FIGS. 1A-1C, the chassis 12 includes an inner, body facing surface 532, and an outer, garment facing surface 534. As shown in FIG. 1C, the chassis 12 may include a topsheet 538 forming a portion of the body facing surface 532. The chassis 12 may also include a backsheet 540 formed from a laminate including an outer covering layer and an inner layer. An absorbent core 542 may be disposed between a portion of the topsheet 538 and the backsheet 540. The chassis 12 may also include leg elastics 544, such as shown in FIG. 1C, and an elastic waist region to enhance the fit around the legs and waist of the wearer. Example leg elastic and leg cuff embodiments are disclosed in, for example, U.S. Pat. Nos. 4,695,278 and 4,795,454. It is to be appreciated that any one or more of the regions of the chassis may be stretchable and may include various types of elastomeric materials and/or laminates. As such, the diaper may be configured to adapt to a specific wearer's anatomy upon application and to maintain contact with the wearer's anatomy during wear.

As previously mentioned, the chassis 12 may include a backsheet 540, shown for example, in FIG. 1C. The backsheet may also define the outer surface 534 of the chassis 12. In some embodiments, the backsheet may be configured to prevent exudates absorbed and contained within the chassis from soiling articles that may contact the diaper, such as bedsheets and undergarments. Certain backsheet embodiments may be fluid permeable, while other embodiments may be impervious to liquids (e.g., urine) and include a thin plastic film. Some backsheet films may include those manufactured by Tredegar Industries Inc. of Terre Haute, Ind. and sold under the trade names X15306, X10962, and X10964. Other backsheet materials may include breathable materials that permit vapors to escape from the diaper while still preventing exudates from passing through the backsheet. Exemplary breathable materials may include materials such as woven webs, nonwoven webs, composite materials such as film-coated nonwoven webs, monolithic films and microporous films. Example breathable composite materials are described in greater detail in PCT Application No. WO 95/16746 and U.S. Pat. No. 5,865,823, both of which are hereby incorporated by reference. Other breathable backsheets including nonwoven webs and apertured formed films are described in U.S. Pat. Nos. 5,571,096 and 6,573,423, which are both hereby incorporated by reference.

The backsheet 540 may be formed by only one sheet (or layer) material such as a breathable (or microporous or monolithic) film material or a non-breathable (or non-microporous) film material. In some embodiments, the backsheet may be formed by two (or more) sheet (or layer) materials which may include a non-breathable (or breathable) film material and a nonwoven outer cover material. In some embodiments, the backsheet may be formed by a laminate of two sheet (or layer) materials joined together, for example, the backsheet may include a non-breathable film material forming the inner layer of the backsheet and a nonwoven material forming the outer layer which may be joined to the garment facing surface of the film material to provide a cloth-like and/or garment-like feel. In accordance with the discussion above, graphics may be printed on the film, the nonwoven, or the composite substrate to make printed component material, which may be converted into absorbent articles comprising printed backsheets.

As previously mentioned, the chassis 12 may include a topsheet 538, shown for example, in FIG. 1C. The topsheet 538 may also define a portion of the inner surface 532 of the chassis 12. All or a portion of the topsheet may be liquid pervious, permitting liquid to readily penetrate there through. As such, the topsheet may be manufactured from a wide range of materials, such as porous foams; reticulated foams; apertured nonwovens or plastic films; or woven or nonwoven webs of natural fibers (e.g., wood or cotton fibers), synthetic fibers (e.g., polyester or polypropylene fibers), or a combination of natural and synthetic fibers. One example of a topsheet including a web of staple length polypropylene fibers is manufactured by Veratec, Inc., a Division of International Paper Company, of Walpole, Mass. under the designation P-8. Examples of formed film topsheets are described in U.S. Pat. Nos. 3,929,135; 4,324,246; 4,342,314; 4,463,045; and 5,006,394, all of which are hereby incorporated by reference herein. Other topsheets may be made in accordance with U.S. Pat. Nos. 4,609,518 and 4,629,643, both of which are hereby incorporated by reference.

In some embodiments, the topsheet is made of a hydrophobic material or is treated to be hydrophobic in order to isolate the wearer's skin from liquids contained in the absorbent core. If the topsheet is made of a hydrophobic material, at least the upper surface of the topsheet may be treated to be hydrophilic so that liquids will transfer through the topsheet more rapidly. The topsheet can be rendered hydrophilic by treating it with a surfactant or by incorporating a surfactant into the topsheet. A more detailed discussion of such a treatment and hydrophilicity is contained in U.S. Pat. Nos. 4,988,344 and 4,988,345, both of which are hereby incorporated by reference. A more detailed discussion of some methods for incorporating surfactant in the topsheet can be found in U.S. Statutory Invention Registration No. H1670, which was published on Jul. 1, 1997, in the names of Aziz et al., all of which are hereby incorporated by reference. In some embodiments, the topsheet 138 may include an apertured web or film that is hydrophobic. This may be accomplished eliminating the hydrophilizing treatment step from the production process and/or applying a hydrophobic treatment to the topsheet, such as a polytetrafluoroethylene compound like SCOTCHGUARD or a hydrophobic lotion composition, as described below. A more detailed discussion of various apertured topsheets can be found in U.S. Pat. Nos. 5,342,338; 5,941,864; 6,010,491; and 6,414,215, all of which are hereby incorporated by referenced.

As previously mentioned, the chassis 12 may also include an absorbent core 542. As shown for example in FIG. 1C, the absorbent core 542 may include a first longitudinal side edge 146 laterally separated from a second longitudinal side edge 548, and a first end edge 550 longitudinally separated from a second end edge 552. The absorbent core may also include components such as an acquisition layer and absorbent material that is generally compressible, conformable, non-irritating to the wearer's skin and capable of absorbing and retaining liquids such as urine and other body exudates. The absorbent core can also be manufactured in a wide variety of sizes and shapes (e.g., rectangular, hourglass, T-shaped, asymmetric, etc.). The absorbent core may also include a wide variety of liquid-absorbent materials commonly used in disposable diapers and other absorbent articles. In one example, the absorbent core includes comminuted wood pulp, which is generally referred to as airfelt. Examples of other absorbent materials include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials.

It is to be appreciated that the configuration and construction of the absorbent core may be varied (e.g., the absorbent core(s) or other absorbent structure(s) may have varying caliper zones, a hydrophilic gradient, a superabsorbent gradient, or lower average density and lower average basis weight acquisition zones; or may comprise one or more layers or structures). Exemplary absorbent structures are described in U.S. Pat. Nos. 4,610,678; 4,673,402; 4,834,735; 4,888,231; 5,137,537; 5,147,345; 5,342,338; 5,260,345; 5,387,207; and 5,650,222, all of which are hereby incorporated by reference.

The absorbent core may also have a multiple layered construction. A more detailed discussion of various types of multi-layered absorbent cores can be found in U.S. Pat. Publication Nos. 2004/0162536A1 and 2004/0167486A1; U.S. Pat. Nos. 5,669,894; 6,441,266; 5,562,646; European Pat. No. EP0565606B1; PCT Publication No. WO 2006/015141, which are all hereby incorporated by reference. In some embodiments, the diaper pant includes an absorbent core that is stretchable. In such a configuration, the absorbent core may be adapted to extend along with other materials of the chassis in longitudinal and/or lateral directions. The absorbent core can also be connected with the other components of the chassis various ways. For example, the diaper may include a "floating core" configuration or a "bucket" configuration wherein the diaper includes an anchoring system that can be configured to counteract the forces tending to move the article on the wearer. Such an anchoring system can also be configured to anchor itself to a body of a wearer by contacting various parts of the body. In this way, the anchoring system can balance the collected moving forces with holding forces obtained from the anchoring. By balancing the collected moving forces with the obtained holding forces, the anchoring system can at least assist in holding the disposable wearable absorbent article in place on a wearer.

As discussed above, the absorbent article may include an absorbent core, which may comprise any absorbent material capable of absorbing and retaining liquids such as urine and other body exudates. Exemplary but not limiting absorbent structures for use as the absorbent core are described in U.S. Pat. Nos. 4,610,678, 4,673,402, 4,888,231, and 4,834,735, each herein incorporated by reference. The absorbent core may be manufactured in a wide variety of sizes and shapes (e.g., rectangular, hourglass, "T"-shaped, asymmetric, etc.), and from a wide variety of liquid-absorbent materials commonly used in disposable diapers and other absorbent articles. The absorbent core may also include multiple layers of absorbent material, each having individual liquid acquisition, acquisition/distribution, or storage/redistribution characteristics, as well as individual shape, width, length, and thickness characteristics. The number and placement of absorbent layers may be varied to achieve desired characteristics such as thinness, softness, flexibility, or beneficial liquid acquisition, distribution, and storage rates, as well as capacity and storage rates, wearer comfort, etc. The components or members of the absorbent core may include laminates or combinations of several sheets or webs of materials. In general, the absorbent core may be made of any suitable absorbent material or combination of materials.

Embodiments of the diaper pant may also include pockets for receiving and containing waste, spacers which provide voids for waste, barriers for limiting the movement of waste in the article, compartments or voids which accept and contain waste materials deposited in the diaper, and the like, or any combinations thereof. Examples of pockets and spacers for use in absorbent products are described in U.S. Pat. Nos. 5,514,121; 5,171,236; 5,306,266; 5,397,318; 5,540,671; and PCT Application WO 93/25172; which are all hereby incorporated by reference. Examples of compartments or voids are disclosed in U.S. Pat. Nos. 4,968,312; 4,990,147; 5,062,840; 6,482,191; and 5,269,755, which are all hereby incorporated by reference. Examples of transverse barriers are described in U.S. Pat. Nos. 5,554,142 and 5,653,703; and PCT Patent Publication WO 94/14395, which are all hereby incorporated by reference. In addition to or in place of the voids, pockets and barriers, described above, embodiments of the absorbent article may also include a waste management element capable of effectively and efficiently accepting, storing and/or immobilizing viscous fluid bodily waste, such as runny feces, such as described in U.S. Pat. No. 6,010,491, which is hereby incorporated by reference.

Figure 1D:
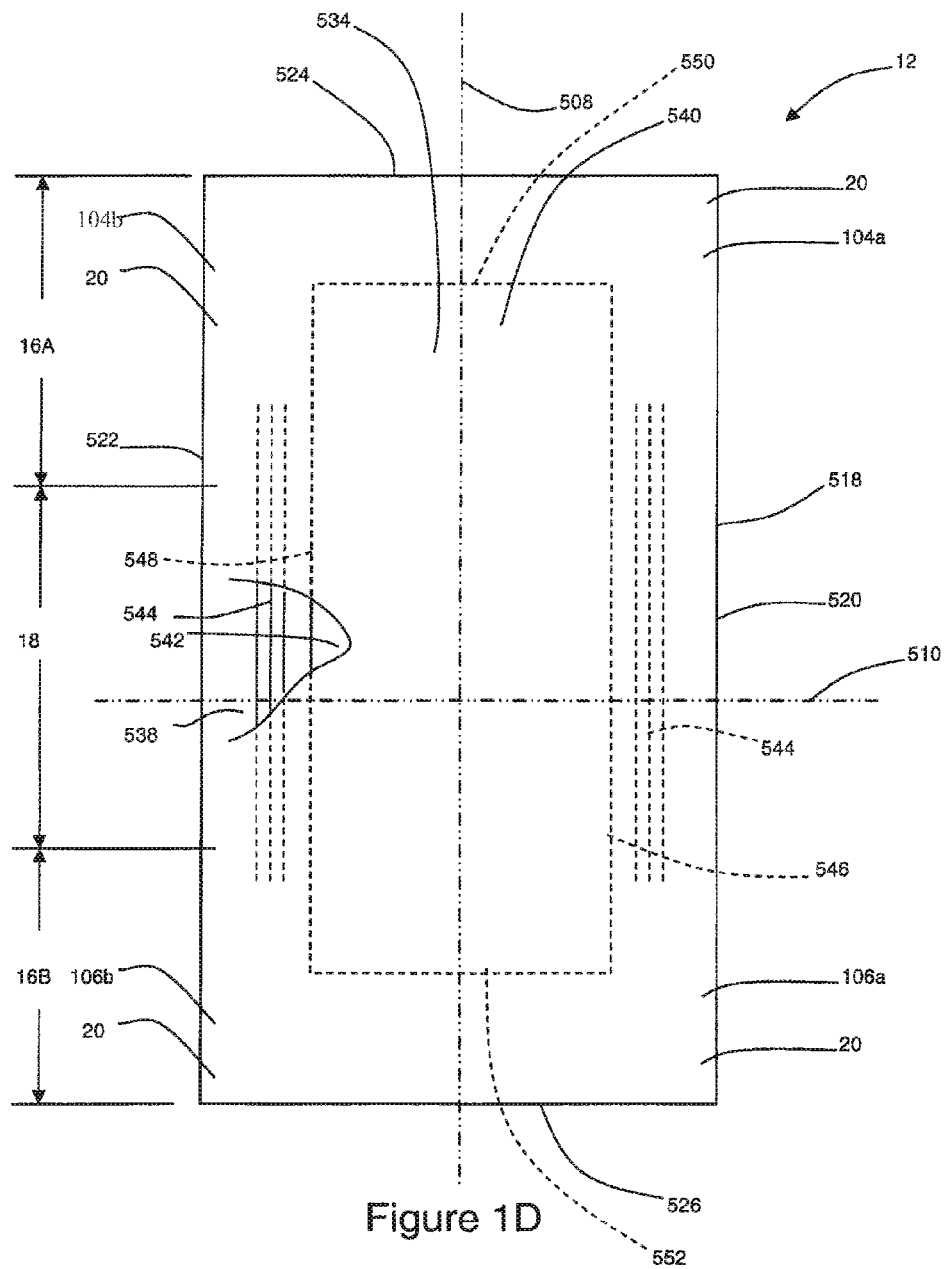
FIG. 1D is a partially cut away plan view of a second embodiment of a diaper chassis.

As discussed in more detail below and as shown in FIG. 1C, the first and second waist regions 16A, 16B of the chassis 12 may include distal end regions or ears 20, also referred to as first ears 104a, 104b and second ears 106a, 106b that connect the first waist region 16A and the second waist region 16B with side panels 14A, 14B to form the waist opening 21 and two leg openings 22. The first ears 104a, 104b each include proximal regions connected with the first waist region 112 of the chassis 102. And second ears 106a, 106b each include proximal regions connected with the second waist region 114 of the chassis 102. Distal regions of the first ear 104a and the second ear panel 106a may be connected or fastened to the first side panel 14A, and distal regions of the first ear 104b and the second ear 106b may be connected or fastened to the second side panel 14B. It should be appreciated that the ears 20 may be formed as continuous extensions of one or both the first and second waist regions of the chassis. It should also be appreciated that the chassis 12 may have a perimeter 518 defining a rectangular shape, such as shown in FIG. 1D, wherein the ears 20 are defined by regions of the chassis 12 extending adjacent the first and second longitudinal side edges 520, 522 in the first and second waist regions 16A, 16B.

Figure 3:
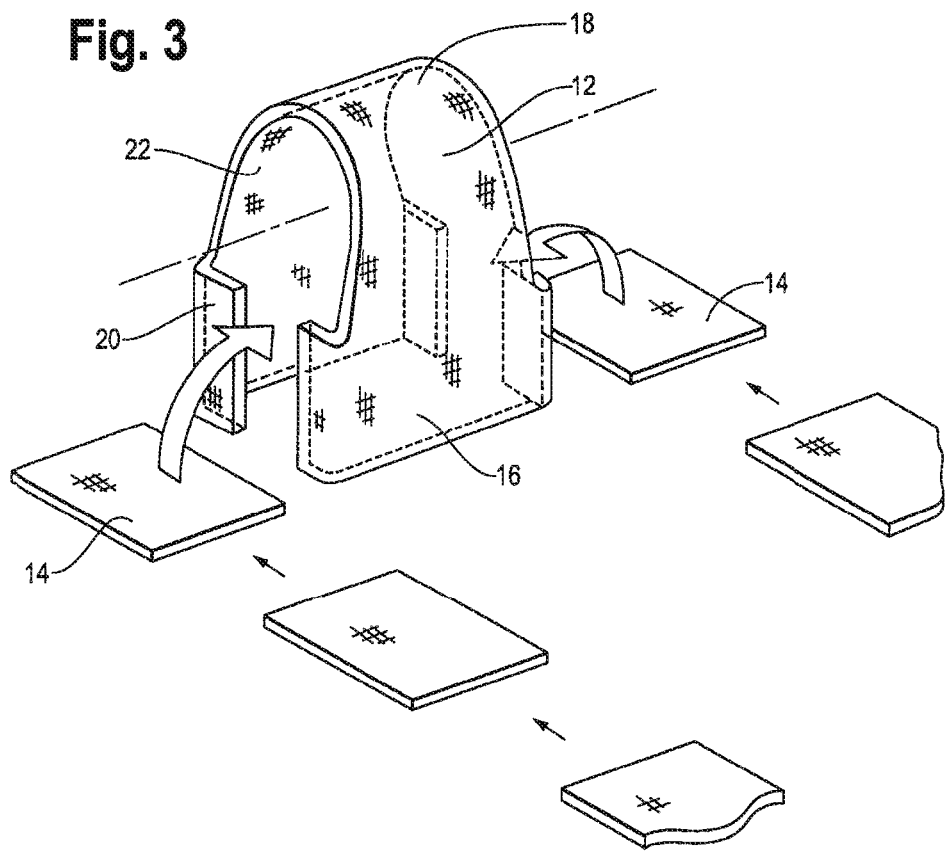
FIG. 3 is a perspective, simplified exploded view of a diaper pant in the process of being constructed in accordance with the teachings of a first embodiment of the present disclosure.

Referring now to FIGS. 1A-5, an absorbent article or diaper pant 10 constructed in accordance with the teachings of the present disclosure is illustrated. As previously mentioned with reference to FIG. 1, embodiments of the diaper pant 10 may include first and second side panels 14A, 14B that connect the first waist region 16A with the second waist region 16B of the chassis 12 to form the waist opening 21 and two leg openings 22. The diaper pant 10 includes a chassis 12 and side panels 14. A plurality of chassis 12 may be provided in a web 13, and formed in a machine direction (MD), as illustrated in FIG. 2. The ears 20 are folded at an angle to the waist regions 16A, 16B. As previously mentioned, the first ear 104a and second ear 106a are connected with first side panel 14A along two seams 24, and the first ear 104b and second ear 106b are connected with second side panel 14B along two seams 24. As illustrated in FIG. 3, the diaper pant 10 may be formed in an assembly line process, where the side panels 14 are formed from a web of material that is separate from the chassis 12. Once the chassis 12 is formed and the ears 20 are turned at an angle to the waist region 16, the side panels 14 are brought along side of the chassis 12 and turned into alignment with the ears 20 (e.g., the side panels 14 are positioned parallel to the ears 20) as illustrated in FIGS. 1A and 3-5A. The seams that are formed simultaneously may be a combination of different seam types described herein, such as a thermal seam on the back side of the chassis and a hook-and-loop type seam at the front side of the chassis. More specifically, the seams may be formed by one of adhesives, cohesives, hook and loop fasteners, thermal bonding, pressure bonding, ultrasonic bonding, or a combination thereof.

Figure 4:
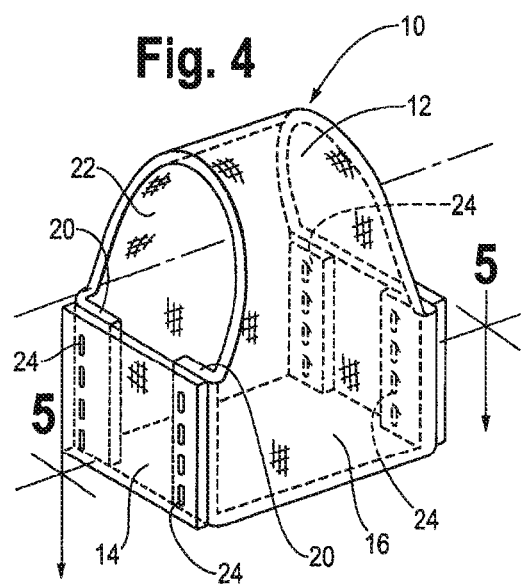
FIG. 4 is a perspective view of the diaper pant of FIG. 3 in a fully assembled configuration.
Figure 5A:
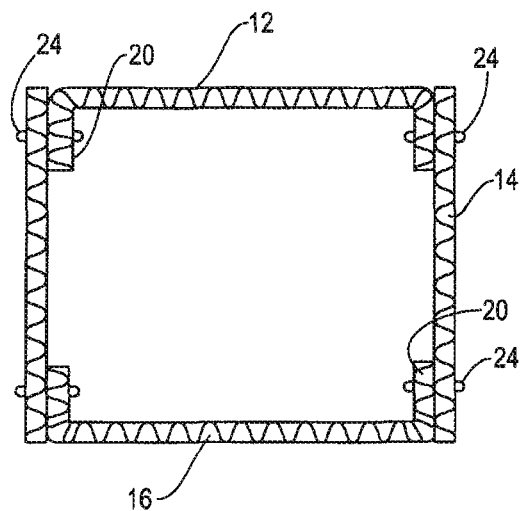
FIG. 5A is a top cross-sectional view of the diaper pant of FIG. 4, taken along lines 5-5 of FIG. 4.
Figure 5B:
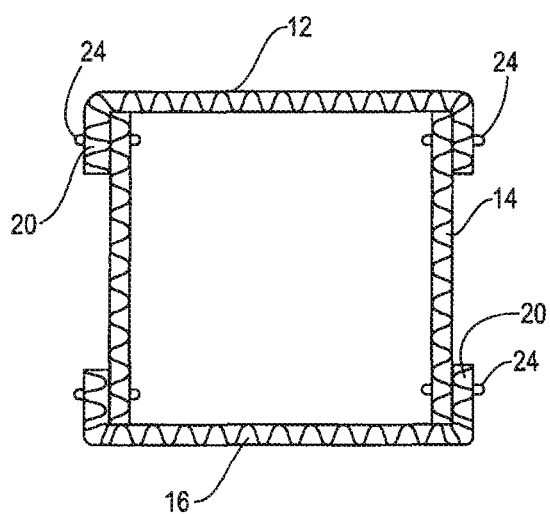
FIG. 5B is a top cross-sectional view similar to that of FIG. 5A, but of the diaper pant illustrated in FIG. 1B.

Alternatively, the side panels 14 may be brought along side of the chassis 12 before turning the ears 20 at an angle to the waist region 16, as illustrated in FIGS. 1B and 5B. Once aligned with the ears 20, the side panels 14 are connected to the ears 20 simultaneously, or substantially simultaneously, along four seams 24 (FIGS. 4, 5A, 5B). Various methods of connecting the side panels 14 to the ears 20 may be used. For example, the side panels 14 may be connected with the ears 20 by adhesives, cohesives, hook and loop fasteners, thermal bonding, pressure bonding, ultrasonic bonding, etc. Once the side panels 14 are attached to the chassis 12, the diaper pant 10 is substantially completely formed, although minor seam inspection and side panel/chassis edge tucking operations may be completed later (i.e., downstream). As illustrated in FIGS. 1A, 4 and 5A, the side panels 14 are disposed laterally outward of the ears 20 in this embodiment. In the configuration illustrated in FIGS. 1A, 2-5A, substantially flat sheets may be used as the side panels 14. As a result, relatively less effort may be required to secure the side panels 14 to the chassis 12, and the entirety of the chassis 12, including the ears 20, as well as the entirety of the side panels 14, can be supported throughout the seaming process (as contrasted with conventional diaper assembly operations, in which it was common for at least a portion of the chassis, particularly in the area of overlapping or butt-type seams, to be left to float freely during at least a portion of the seaming operation or at immediately prior to seaming, limiting the speed of assembly equipment and size of material employed in diaper manufacture, so as to avoid misfeeds, jams, entanglements, and other detrimental effects of loose, floating chassis side panels during diaper manufacture).

Various types of articles, such as those discussed above with reference to FIGS. 1-5, may be produced in accordance with the methods and apparatuses disclosed herein. In some embodiments, a continuous web may be cut into individual blanks, and the individual blanks are transferred to a processing wheel. More particularly, the individual blanks are transferred to corresponding processing stations moving along an orbit path as the processing wheel rotates. As the processing stations move along an orbit path, the processing stations may perform various operations, such as folding the blanks, superimposing sealing areas on the folded blanks, and sealing the side panels to form individual absorbent articles.

With reference to FIGS. 6-9, a description of various types of articles that may be produced in accordance with the methods and apparatuses disclosed herein is provided below to provide a context for subsequent descriptions relating to the operation and structural features embodiments of the processing wheel and processing stations and associated manufacturing processes. Although the following description refers to disposable absorbent articles, in which a diaper chassis and one or more side panels are combined to form an absorbent article, it is to be appreciated that various types of articles may be produced in accordance with the methods and apparatuses described herein. As such, absorbent articles referred to herein may include a single layer or multiple layers of woven or nonwoven material and may include a thermoplastic film.

Figure 6:
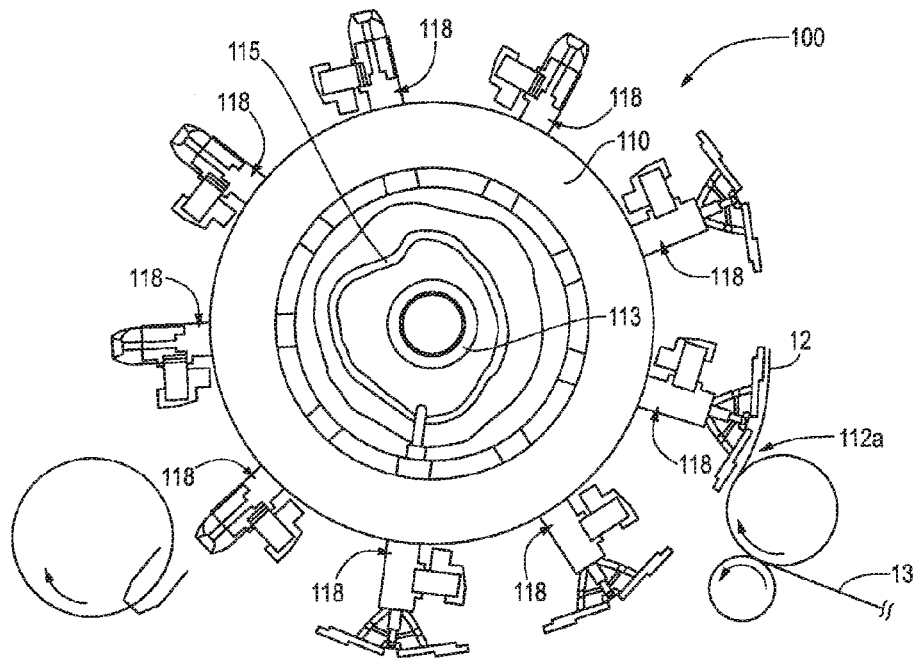
FIG. 6 is a side view, partially cut away, of a one embodiment of a machine that assembles diaper pants according to certain embodiments disclosed herein.

FIGS. 6-10 illustrate one embodiment of a machine 100 that may be used to form the diaper pant 10 of FIGS. 1-3. The machine 100 includes a final folding and seaming machine (FFS). Some examples of FFS apparatuses and methods may be found in U.S. Pat. No. 5,779,831 and U.S. Patent Publication No. 2008/0083489, which are both incorporated by reference herein. The machine 100 generally includes a main drum 110, such as a wheel or hub, and a plurality of processing stations 112. As the main drum 110 rotates, the processing stations 112 operate to perform various functions, such as folding the chassis 12 (FIG. 3) in preparation for registration and receipt of the side panels 14 (FIG. 3), as well as seaming of the side panels 14 to the chassis 12. As illustrated in FIG. 6, as the main drum 110 rotates, the individual processing stations 112 move from a receiving location where articulating arms 114 are extended (as illustrated for example near the bottom right of FIG. 6) to a folding location wherein the articulating arms 114 are retracted (as illustrated for example near the top left of FIG. 6). As discussed in more detail below, as the processing stations 112 move through the folding location, the processing stations 112 actuate and fold the individual chassis 12 along one or more lateral axes. The processing stations 112 may fold the chassis 12 in more than one direction, such as along a transverse axis to form a U-shape of the diaper pant 10 and along gripping members 116 (FIG. 7) to position the ears 20 for engagement with the side panels 14.

As the main drum 110 continues to rotate, the processing stations 112 move from the folding location to a sealing location. As the processing stations 112 move through the sealing location, the processing stations 112 engage the side panels 14 and the ears 20 to form the side seams 24 (FIG. 5). The main drum 110 continues to rotate and the processing stations 112 move from the sealing location to a discharge location, where the folded diaper pants 10 are removed from the main drum 110. As the processing stations 112 move along the sealing location, the side seams are formed. As discussed above, the side seams may be formed with various types of connection methods, including for example, pressure bonding, ultrasonic bonding, heat sealing, adhesive attachment, and mechanical attachment. As such, in some arrangements, such as when forming absorbent articles with resealable side seams utilizing, for example, adhesives or mechanical attachments, pressure may be applied to the sealing area to form the side seams. In other arrangements, a heat exchanger and a compression tool may be used to form the side seams. In some embodiments, the heat exchanger forces hot air against the folded blanks, and the compression tool presses the side seams. In some embodiments, cool air may also be applied to the folded, seamed blanks to cool the blanks during compression. It is to be appreciated that depending on the particular configuration, heating and cooling times for the side seam material may vary. It should also be appreciated that FIG. 6 is merely an exemplary representation of an embodiment, and the positions and durations of some process steps may vary and/or may overlap, such as the receiving, folding, sealing, and discharge locations.

Figure 7:
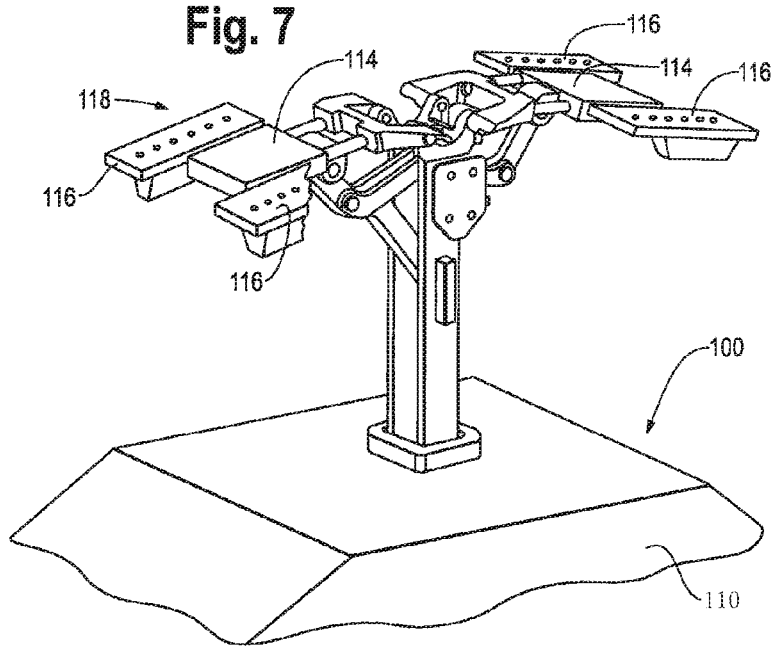
FIG. 7 is a perspective view of one of the articulator arms of the machine of FIG. 6.

As previously mentioned, the main drum 110 includes a plurality of processing stations 112. For example, the main drum 110 illustrated in FIG. 6 includes nine processing stations 112. It should be appreciated that the main drum 110 may include more or fewer processing stations 112 than illustrated herein. For example, some embodiments may include six (or even fewer) processing stations 112 and some embodiments may include as many as twelve (or more) processing stations 112. As discussed above, the processing stations 112 perform various operations as the main drum 110 rotates. For example, individual chassis 12 disposed on respective processing stations 112 are folded as the main drum 110 rotates. As such, each processing station 112 may include a folding mechanism 118 upon which an individual chassis 12 is disposed as the main drum 110 rotates. One embodiment of a folding mechanism 118 is shown in FIGS. 6-8. In particular, FIG. 7 illustrates a perspective view of the folding mechanism 118 on the main drum 110, FIG. 8 illustrates a side view of the folding mechanism 118 with articulating arms 114 in an extended position; and FIG. 7 illustrates a cross sectional view of the folding mechanism 118 with articulating arms 114 in a retracted position.

As illustrated in FIGS. 7-9, the folding mechanism 118 includes gripper members 116 which hold the chassis 10 while the main drum 110 rotates. More particularly, with reference to FIGS. 6-9, the individual chassis 10 are transferred from the folding mechanism 118 such that the gripper members 116 are brought into contact with the chassis 12. Each gripper member 116 may be configured with a vacuum that exerts a holding force on the chassis 12. The arc length from a leading end of a first pair of gripper members 116 at a first end of the folding mechanism 118 to a trailing end of the second pair of gripper members 116 associated with that same folding mechanism 118 is substantially equal to the length of a single chassis 12, and as a plurality of chassis 12 is fed to the machine 100 along a web 13 (see lower right portion of FIG. 6), the chassis 12 are cut into such lengths, such as by one or more blades on a cutting wheel 15, in a cutting operation immediately upstream of the folding mechanism 118 at the processing station 112a.

The gripper members 116 are configured not only to accept and retain a chassis 12, but also to rotate and move to fold the chassis 12. In particular, the chassis 12 is delivered to the folding mechanism 118 at processing station 112a when the articulating arms 114 are in the extended position (FIGS. 7, 8) and the gripper members 116 hold the chassis 12 on the folding mechanism 118. As the articulating arms 114 retract (FIG. 9), the chassis 12 is folded about the crotch region 18 and the gripper members 116 rotate approximately 90 degrees about an axis of the respective articulating arm 114 of the folding mechanism 118 during the retraction phase to fold the ears 20 relative to the waist region 16 of the chassis 12.

The extension and retraction of the articulating arms 114 during rotation of the main drum 110 may be controlled via a cam mechanism. The folding mechanism 118 may include one or more rollers 117, 119 located within the main drum 110, the rollers riding within cam tracks 113, 115 within the main drum 110. The rollers 117, 119 and cam tracks 113, 115 cooperate to extend and retract the articulating arms 114 as well as operate paddles on auxiliary drums, as will be discussed further below.

As illustrated in FIG. 10, the main drum 110 includes first and second smaller diameter auxiliary drums 130, such as a wheels or hubs, delivering the side panels 14 to the folded chassis 12. An example of auxiliary drums may be found in International Patent Application No. WO 00/41664, which is incorporated by reference herein. Each of the first and second auxiliary drums 130 is coaxially aligned with the main drum 110. Each of the auxiliary drums 130 includes a plurality of side panel stations 132. The number of side panel stations 132 may correspond to the number of processing stations 112. Each side panel station 132 includes a pivotably mounted transfer element, such as an articulating paddle 134 rotatably attached to the auxiliary drum 130. The articulating paddles 134 rotate about axis A from a receiving position that is substantially parallel to an axis of rotation X of the main drum 110 to a delivering position that is substantially perpendicular to the axis of rotation X. Each of the articulating paddles 134 may include a vacuum system to releasably hold the side panels 14 on the articulating paddles 134. The side panels 14 may be delivered to a respective auxiliary drum 130 as a continuous web 136 of material. A knife wheel 140 may cut the continuous web of material 136, thereby forming individual side panels 14 before the individual side panels 14 are delivered to the articulating paddles 134. After the side panel 14 is delivered to an articulating paddle 134, the articulating paddle 134 rotates about axis A to the delivering position (for example, as illustrated by the articulating paddle 134 near the top of the auxiliary drum 130), in which the articulating arms 114 of the folding mechanism 118 are in their refracted orientation, as illustrated in FIG. 9.

The articulating paddles 134 may be actuated via the camming mechanism in the main drum 110. A cam (not shown) may be located within the respective auxiliary drum 130 to selectively engage an oscillating mechanism (not shown). The oscillating mechanism is provided with a rack that cooperates with a pinion linked to the articulating paddle 134. The cam mechanism that controls movement of the articulating paddles 134, as well as the cam mechanism that actuates the articulating arms 114 of the folding mechanism 118, may be driven by a drive shaft, actuated by a drive motor (not shown) that imparts rotation to the main and auxiliary drums 110, 130. Because the gripper arms 116 of the folding mechanism 118 have already rotated 90 degrees about the axis of the respective articulating arm 114, thereby folding the ears 20 relative to the waist region of the chassis 12, the ears 20 are ready to receive the side panels 14. After the side panel 14 is brought into register with the ears 20 by the articulating paddle 134, the side panel 14 is connected with the ears 20 by a seaming mechanism (not shown). The seaming mechanism may be included in the articulating paddle 134 (as a heating element, for example), such that seaming operations are performed simultaneously with, or very shortly after, registration of the side panel 14 with the folded ears 20. Alternatively, the seaming mechanism may be a completely separate device and the side panel 14 may be held in position by the vacuum system of the folding mechanism 118 until seaming operations are completed. Regardless, once the side panels 14 are positioned with respect to the chassis 12, the side panels 14 may be connected and seamed to the ears 20 at four locations simultaneously, or substantially simultaneously. After the side panels 14 are seamed to the ears 20, the diaper pant 10 may be removed from the folding mechanism 118 by a moving conveyor, gravity, or any known means.

FIG. 11 is a logic flow diagram illustrating a process 200 for making the diaper pant 10 of FIG. 1. The process 200 initially begins with parallel operations 210 and 220. The chassis 12 is formed in a chassis formation process 210 separately from the side panels 14, which are formed in side panel processes 220. The chassis forming process 210 begins at 212 with formation of a chassis web by laminating two or more layers of material (at least one absorbent layer and at least one non-woven layer) together to form a continuous web of material. The chassis web is fed into a cutting device where the chassis web is cut into discrete chassis 12 with a final knife cut at 214. From there, the discrete chassis 12 are transferred onto a final folder and seamer (FFS) at 216. Once on the FFS, the discrete chassis 12 are bi-folded to form the chassis 12 with bent ears 20, as illustrated in FIG. 3, at 218.

Concurrently with the chassis formation process 210, the side panels 14 are each formed in a side panel process 220. However, the side panel process 220 need not take place at the same time as the chassis formation process 210. In other embodiments, the side panel process 220 may occur before or after (i.e., upstream or downstream of) the chassis formation process 210. In yet other embodiments, the side panel process 220 may partially overlap in time with the chassis formation process 210. Regardless, the side panel process 220 begins with providing a stretch laminate at 222. The side panels 14 may be shaped and/or separated at 224 through die cutting and trim removal, or other known processes to shape and separate the side panels 14. The side panels 14 may be cut to size from a continuous web of stretch laminate, or the side panels 14 may be separated from a pre-scored web of stretch laminate. Once shaped and/or separated, the side panels 14 are transferred onto the FFS at 226, where the side panels 14 are rotated and/or moved into register with the chassis 12 at 228.

Once the side panels 14 are placed in register with the chassis 12 (FIG. 2), the side panels 14 are attached to the chassis 12 along the four seams 24 (FIG. 3) at 230. The four seams 24 may be formed simultaneously, or substantially simultaneously, thereby increasing the efficiency and speed of the diaper pant formation process 200. After the diaper pant 10 is fully formed, the diaper pant 10 is discharged from the FFS at 232, the seams 24 may be inspected at 234 for quality control, and the ears 20 and/or side panels 14 are tucked if needed at 236. Example methods and apparatuses for side panel tucking are disclosed in U.S. Provisional Patent Application Nos. 61/322,349 and 61/322,338, both filed on Apr. 9, 2010; as well as U.S. Pat. Nos. 6,723,035 and 6,776,316, all incorporated herein by reference.

One embodiment of the diaper assembly process disclosed herein generally includes the steps of (1) folding the chassis 12; (2) folding the ears 20; (3) applying the side panels 14; and (4) seaming the side panels 14 to the chassis 12, without any intervening steps (i.e., the diaper chassis and side panels remain affixed to conveying elements of the FFS until the processes of folding the chassis, folding the ears, applying the side panels, and seaming are complete, and no separate equipment other than the FFS performs any manipulation of the diaper chassis or side panels in between the steps of folding the chassis 12, folding the ears 20, or applying the side panels 14). However, the step of folding the chassis 12 and the step of folding the ears 20 may be reversed in some embodiments.

Figure 12:
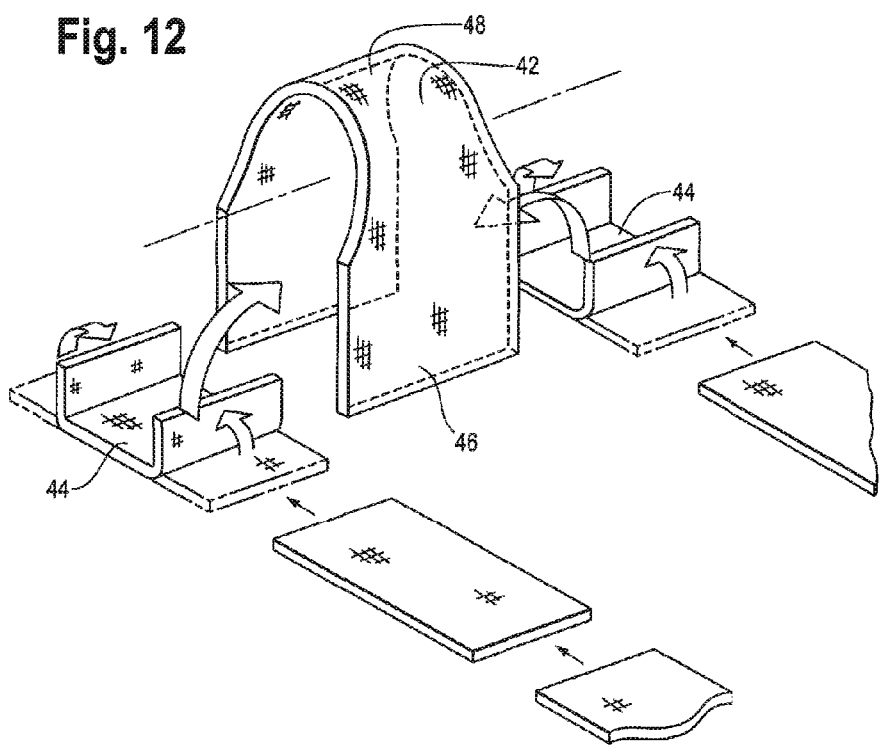
FIG. 12 is a perspective, simplified exploded view of a diaper pant constructed in accordance with a third embodiment of the present disclosure.
Figure 13:
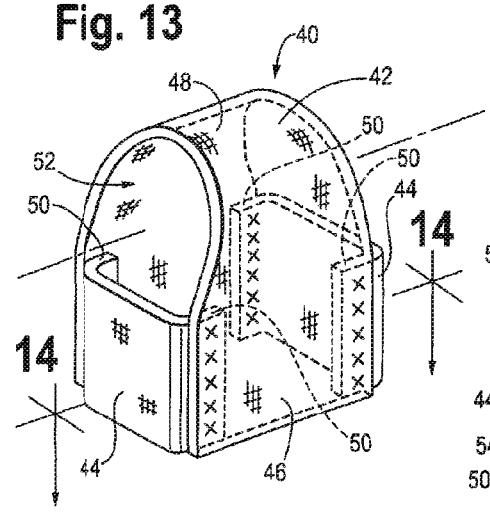
FIG. 13 is a perspective view of the diaper pant of FIG. 12 in a fully assembled configuration.
Figure 14:
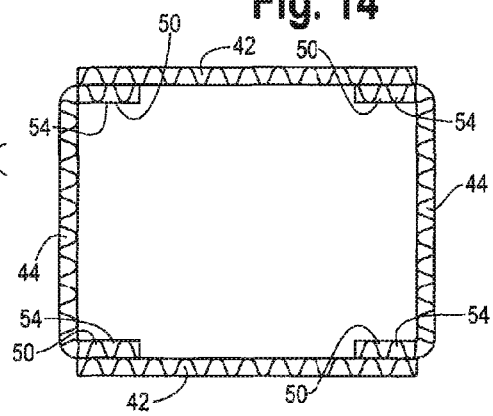
FIG. 14 is a top cross-sectional view of the diaper pant of FIG. 13, taken along lines 14-14 of FIG. 13.

FIGS. 12-14 illustrate a diaper pant 40 constructed in accordance with an alternate embodiment of the present disclosure. The diaper pant 40 comprises a chassis 42 and two side panels 44. The chassis 42 includes waist regions 46 and a crotch region 48. Leg openings 52 are formed between the crotch region 48 and the side panels 44 (FIG. 13). As illustrated in FIG. 12, the diaper pant 40 may be formed in an assembly line process, where the side panels 44 are formed from a web of material that is separate from the chassis 42. Once the chassis 42 is formed, the side panels 44 are brought along side of the chassis 42 and turned substantially perpendicular to the waist region 46. Ends of the side panels 44 may be folded inwardly forming one or more side panel edges 50 on each side panel 44. The side panel edges 50 are substantially parallel to the waist region 46. The side panel edges 50 simultaneously, or substantially simultaneously, are attached to the chassis 42 along four seams 54 (FIG. 14). Various methods of connecting the side panels 44 to the chassis 42 may be used. For example, the side panels 44 may be connected with the chassis 42 by adhesives, cohesives, hook and loop fasteners, thermal bonding, pressure bonding, ultrasonic bonding, etc. Once the side panels 44 are attached to the chassis 42, the diaper pant 40 is substantially completely formed. As illustrated in FIGS. 13 and 14, the side panel edges 50 in this embodiment are disposed inside the chassis 40. In the configuration of the diaper pant 40 illustrated in FIGS. 12-14, chassis 42 may not need to include folded ears (like the embodiment of FIGS. 1A, 2-3). As a result, the folding mechanism used to fold the chassis 42 may be simplified.

FIGS. 15-18 illustrate one embodiment of a machine 300 that may be used to form the diaper pant 40 of FIGS. 12-14. The machine 300 will be referred to herein as the mandrel machine 300. The mandrel machine 300 includes a drum or wheel 310 with a plurality of processing stations 312. Each processing station 312 includes a mandrel 314. Each mandrel 314 includes an outer side 316 and an inner side 318. The outer and inner sides 316, 318 have cross-sectional shapes that are curved in an arc of a circle, with the outer side 316 having a generally larger radius of curvature than the inner side 318. The outer and inner sides 316, 318 are joined at a leading side by a generally curved leading surface 320. The outer and inner surfaces 316, 318 are joined at a trailing side by a generally flat trailing surface 322. Each mandrel also has two substantially flat side walls 324. The trailing surface 322 of each mandrel 314 is joined to the wheel 310 by a spoke 326. The wheel 310 rotates in a counter clockwise direction in FIGS. 15 and 17. In other embodiments, or in other views, the wheel 310 may rotate in a clockwise direction. The mandrels 314 may include a vacuum system to hold parts of the diaper pant 40 on the mandrel during different phases of assembly. A web of material 336 is delivered to the mandrel machine 300 via a plurality of side panel rollers 340. The side panel rollers 340 may supply the side panels 44 from the web of material 336. In some embodiments, the side panel rollers 340 may cooperate with one or more knife edges, such as provided on cutting rollers 341 that rotate in a direction opposite to the side panel rollers 340 and bias against the surface of the respective side panel roller 340 so as to cut the web of material 336 into discrete side panels 44. In other embodiments, the web of material 336 may be provided to the side panel roller 340 with pre-formed perforations so that the side panel roller 340 simply separates the discrete chassis 42. Chassis 42 are delivered to the mandrel machine 300 via a conveyor belt 342 at processing station 312a (in the 9:00 position in FIGS. 15 and 17). The conveyor belt 342 delivers the diaper chassis 42 to the processing stations 312 in a feed direction as indicated by the arrow in FIGS. 15 and 17. The conveyor belt 342 may be a fixed speed and unidirectional conveyor belt. Additional conveyor belts 343 are disposed radially inwardly of the mandrels 336 (i.e. downstream of the gap 350 in the direction in which the chassis 12 are fed to the wheel 310) and are spaced laterally apart from one another a sufficient distance to provide clearance such that the spokes 326 can pass between those conveyor belts 343. Additionally, while the conveyor belt 342 is uni-directional, as indicated by the single-headed arrow in each of FIGS. 15 and 17, the conveyor belts 343 are bi-directional as indicated by the double-headed arrows in FIGS. 15 and 17. The conveyor belts 343 may travel in the feed direction before the mandrel 314 contacts the chassis 42 and in an opposite direction after the mandrel 314 contacts the chassis 42 in order to prevent excess frictional wear on the chassis 42 and to produce a proper amount of tension on both sides of the chassis 42 both immediately prior to, and while the chassis 42 is deposited on the mandrel 314. The conveyor belts 343 may also, or alternatively, be variable speed.

As each mandrel 314 passes the side panel rollers 340 (FIGS. 15, 16), discrete side panels 44 are deposited on trailing portions of the mandrel 314 when the mandrel 314 is in a side panel deposit station (as illustrated, for example, near the top of the wheel 310 in FIG. 13). The vacuum system in the mandrel 314 holds each side panel 44 in position and folds the side panel 44 into substantially a U-shape with the side panel 44 being partially disposed on the outer surface 316, the inner surface 318, and the side wall 324. The mandrel may include a plurality of vacuum holes 370 in the outer surface 316, the inner surface 318, and the side walls 324.

As the chassis 42 approach the wheel 310, a leading edge of the chassis crosses a gap 350 in between the conveyor belt 342 and the conveyor belts 343. The gap 350 is large enough for the mandrel 314 to pass through. The gap defines the processing station 312a which may be referred to herein as a chassis mounting station. As the mandrel 314 passes through the gap 350, the leading edge 320 of the mandrel 314 contacts a portion of the chassis 44 that will form the crotch region 48 of the chassis 44. As the mandrel 314 moves further through the gap 350, the chassis 42 conforms to the outer surface 316 and the inner surface 318 of the mandrel 314. In doing so, the waist region 46 of the chassis 42 overlays the side panel edges 50 of the side panels 44. After moving through the gap 350, the chassis 42 is joined to the side panel edges 50 simultaneously, or substantially simultaneously, along four seams 54 (FIG. 14) by a seamer 360 comprising one or more seaming wheels 362. The seaming wheels 362 may incorporate pressure, heat, ultrasound, or any combination thereof in forming the seams 54. After the seams 54 are complete, in order to eject the now-formed diaper pant 40 from the mandrel 314, the mandrel 314 approaches another conveyor belt 370 that is moving at a speed greater than the speed of the mandrel 314. As the diaper pant 40 contacts the conveyor belt 370, the diaper pant 40 is pulled off of the mandrel 314 and delivered downstream for further processing (such as folding end flaps)

Figure 19:
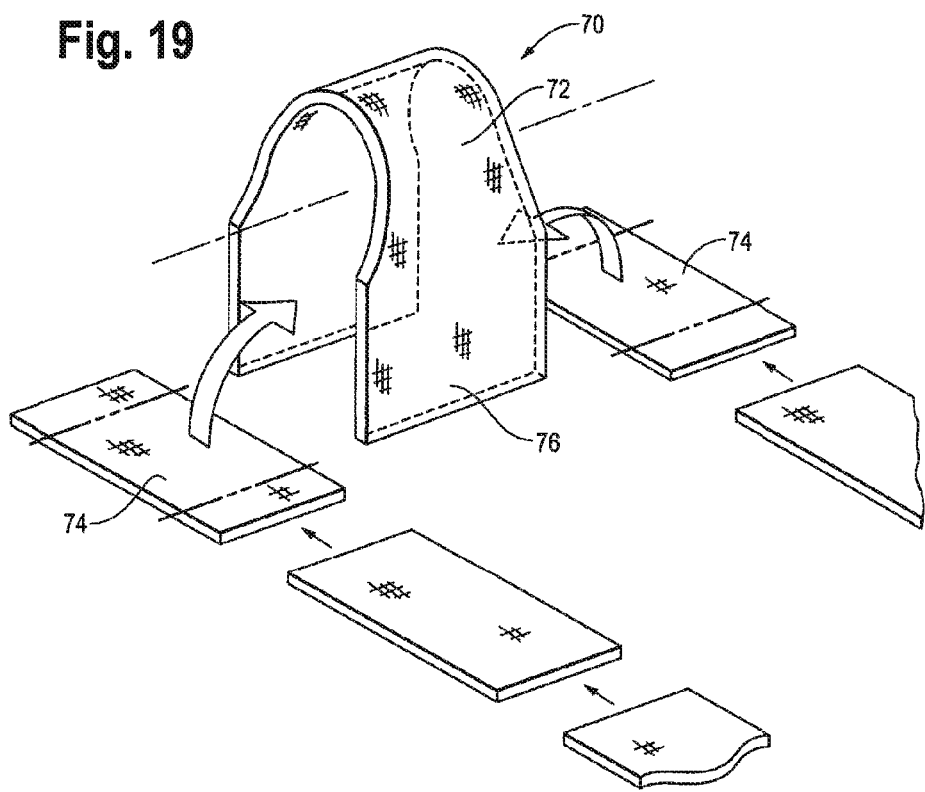
FIG. 19 is a perspective exploded view of a diaper pant constructed in accordance with a fourth embodiment of the present disclosure.
Figure 20:
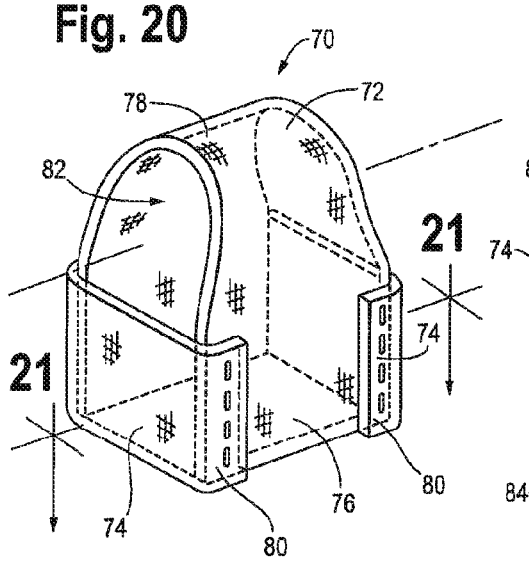
FIG. 20 is a perspective view of the diaper pant of FIG. 19 in a fully assembled configuration.
Figure 21:
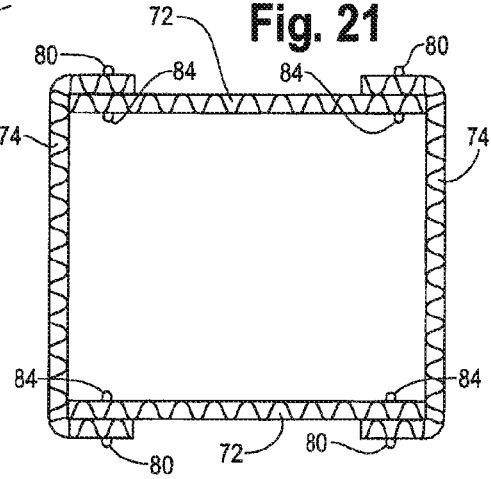
FIG. 21 is a top cross-sectional view of the diaper pant of FIG. 20, taken along lines 21-21 of FIG. 20.
Figure 22:
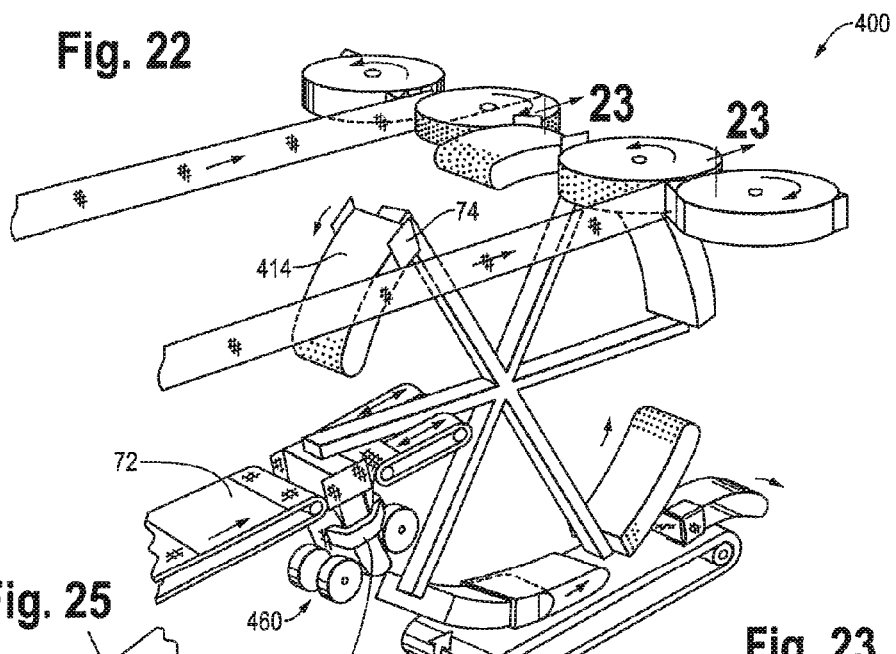
FIG. 22 is a perspective view of a modified embodiment of a machine that assembles diaper pants illustrated in FIGS. 19-21.
Figure 25:
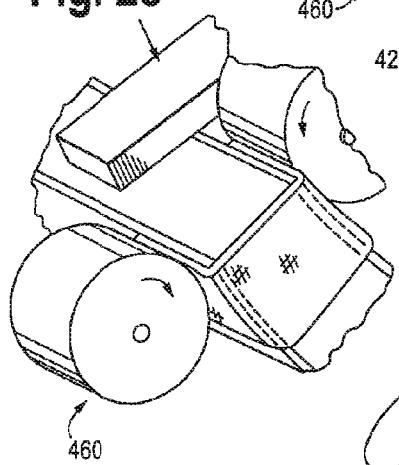
FIG. 25 is an enlarged perspective view of one of the mandrels of the machine of FIG. 22 as a trailing end of the mandrel is passing between securing rollers.
Figure 23:
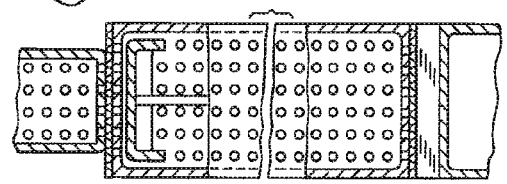
FIG. 23 is a cross-sectional view taken along lines 23-23 of FIG. 22.
Figure 24:
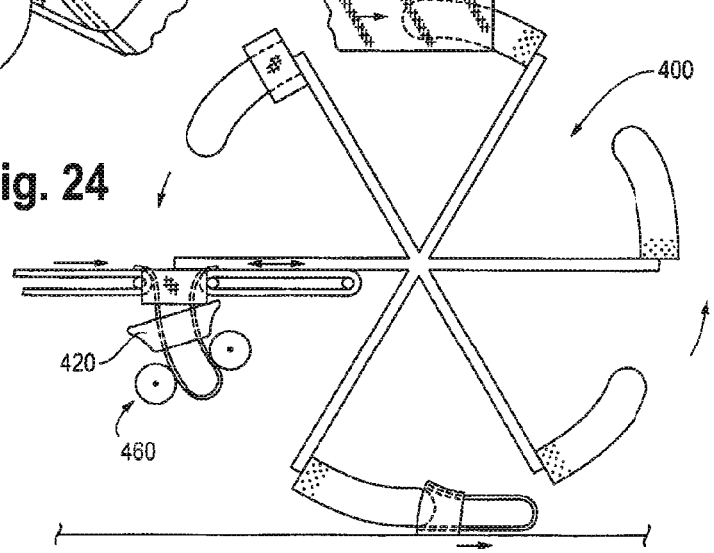
FIG. 24 is a side view of the machine of FIG. 22.

FIGS. 19-21 illustrate another alternate embodiment of a diaper pant 70 constructed in accordance with another embodiment of the present disclosure. The diaper pant 70 comprises a chassis 72 and two side panels 74. The chassis 72 includes waist regions 76 and a crotch region 78. Leg openings 82 are formed between the crotch region 78 and the side panels 74 (FIG. 18). As illustrated in FIG. 17, the diaper 70 may be formed in an assembly line process, where the side panels 74 are formed from a web of material that is separate from the chassis 72. Once the chassis 72 is formed, the side panels 74 are brought along side of the chassis 72 and turned substantially perpendicular to the waist region 76. Ends of the side panels 74 may be folded inwardly, forming one or more side panel edges 80. The side panel edges 80 are substantially parallel to the waist region 76. The side panel edges 80 simultaneously, or substantially simultaneously, are attached to the chassis 72 along four seams 84 (FIG. 21). Virtually any method of seaming the side panels 74 to the chassis 72 may be used. For example, the side panels 74 may be seamed to the chassis 72 by adhesives, cohesives, hook and loop fasteners, thermal bonding, pressure bonding, ultrasonic bonding, etc. Once the side panels 74 are attached to the chassis 72, the diaper pant 70 is substantially completely formed. As illustrated in FIG. 21, the side panel edges 80 in this embodiment are disposed outside the chassis 72. In the configuration illustrated in FIGS. 19-21, the chassis 72 may not need to include folded ears (like the embodiment of FIGS. 1A, 2-3). Thus, the folding mechanism used to fold the chassis 72 may be simplified, because the gripper members 116 would not have to include portions that rotate relative to the axis of the articulating arms 114 while retracting to impart such chassis edge forming folds. However, the paddles 134 of the device shown in FIG. 11 may need to be modified with end portions that rotate to form the side panel edges 80 in this embodiment. Alternatively, the diaper pant 70 illustrated in FIGS. 19-21 may be formed in a mandrel machine 400 as illustrated in FIGS. 22-25, by waiting to fold the side panel edges 80 against the outer surface 416 and inner surface 418 of the mandrel 414 until after the chassis 72 is picked up by the mandrel 414. Additional variations may be necessary, such as providing an side panel folding unit 420 immediately upstream of the seaming station 460. As a further alternative, a mandrel machine may be rearranged by switching relative locations of the side panel mounting station and the chassis mounting station as compared to the positions of those stations in the mandrel machine 300 illustrated in FIGS. 15-18. In other words, if the chassis mounting occurs before the side panel mounting, the diaper 70 embodied in FIGS. 19-21 will result, while maintaining control over the side panel edges 80.

It is to be appreciated that various types and configurations of seaming heads and anvils may be used to create the side seams on the absorbent articles. As discussed above, the side seams may be formed with various types of connection methods, including for example, pressure bonding, ultrasonic bonding, heat sealing, adhesive attachment, and mechanical attachment. As such, in some arrangements, such as when forming absorbent articles with resealable side seams utilizing, for example, adhesives or mechanical attachments, the seaming heads may act only to apply pressure to the sealing areas to form the side seams. In another example, the seaming heads may comprise heated elements that contact the anvils under any pressure. In some embodiments, the pressure may be in the range of from about 1 psi to about 104 psi. In other embodiments, side seaming may utilize with hot air. In one example, a heat exchanger is brought close to overlapping material of the blank and blows hot air against the blank. After applying the hot air, seaming heads compress the overlapping sides. Thus, the material of the side portions is heated and compressed to form the side seal. In yet another embodiment, the seaming heads comprise an ultrasonic conductor. The ultrasonic energy imparted to the sealing areas puts the thermoplastic material of the sealing areas in a heat-softened state, such that upon compression of the sealing areas between the anvil and the conductors an overlapping side seam is formed.

Although the above discussion presents a detailed discussion of embodiments of the processing and folding stations, it is to be appreciated that other embodiments of processing stations that may be adapted for use with the methods and apparatuses disclosed herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for assembling disposable diaper pants, each diaper pant comprising a chassis, a first side panel, and a second side panel, each chassis having a longitudinal axis and a lateral axis, and comprising a first waist region longitudinally opposed to a second waist region, and a crotch region longitudinally intermediate of the first and second waist regions, each chassis further comprising: a topsheet, a backsheet, and an absorbent core disposed between the topsheet and the backsheet, the method comprising the steps of:
providing a chassis;
folding the chassis along the lateral axis to position the first waist region into a facing relationship with the second waist region;
providing first and second side panels;
connecting the first and second side panels with the first waist region and the second waist region of the folded chassis along four seams to form a waist opening and a pair of leg openings; and
wherein the four seams are substantially simultaneously produced.

2. The method of claim 1, further comprising forming a plurality of ears.

3. The method of claim 2, further comprising folding the plurality of ears before connecting the side panels with the chassis.

4. The method of claim 3, wherein the side panels overlay the folded ears.

5. The method of claim 1, further comprising forming folded side panel edges by folding a portion of each side panel.

6. The method of claim 5, wherein the folded side panel edges of the first and second side panels overlay the chassis when the side panels are attached to the chassis.

7. The method of claim 5, wherein the chassis overlays the folded side panel edges when the side panels are attached to the chassis.

8. The method of claim 1, wherein the chassis is folded by a folding device having articulating arms.

9. The method of claim 8, wherein the folding device includes gripping portions on the articulating arms, the gripping portions including a vacuum to hold the chassis on the gripping portions.

10. The method of claim 9, wherein the folding device is mounted on a main drum and the side panels are delivered to the folding device by a first auxiliary drum and a second auxiliary drum, the first and second auxiliary drums being axially aligned with the main drum and extending laterally from the main drum on opposite sides thereof, each of the auxiliary drums having a smaller diameter than the main drum.

11. The method of claim 10, wherein the first and second auxiliary drums include at least one articulating paddle.

12. The method of claim 11, wherein the articulating paddle rotates about an axis that is perpendicular to an axis of rotation of the respective auxiliary drum.

13. The method of claim 1, wherein the chassis is folded by a mandrel.

14. The method of claim 13, wherein the mandrel includes an outer surface and an inner surface, the outer and inner surfaces having a cross-sectional shape that is an arc of a circle.

15. The method of claim 14, wherein a radius of curvature of the outer surface is larger than a radius of curvature of the inner surface.

16. The method of claim 13, wherein at least a portion of the mandrel includes a vacuum system.

17. The method of claim 13, wherein the side panels are disposed on the mandrel prior to the mandrel folding the chassis.

18. The method of claim 1, wherein the seams are formed by one of adhesives, cohesives, hook and loop fasteners, thermal bonding, pressure bonding, ultrasonic bonding, or a combination thereof.

* * * * *